United States Patent
Or et al.

(10) Patent No.: US 6,696,494 B2
(45) Date of Patent: Feb. 24, 2004

(54) α-HYDROXYARYLBUTANAMINE INHIBITORS OF ASPARTYL PROTEASE

(75) Inventors: Yat Sun Or, Cambridge, MA (US); Guoqiang Wang, Cambridge, MA (US); John Rougas, Brighton, MA (US); Jude Elizabeth Mathews, Waltham, MA (US); Kate Ryan Muldoon, Brighton, MA (US); Vincent Alfred Boyd, Cypress, MA (US); Jens Werner Eckstein, Arlington, MA (US); Steven Wayne Riesinger, Stoneham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/007,235

(22) Filed: Oct. 22, 2001

(65) Prior Publication Data
US 2003/0207934 A1 Nov. 6, 2003

(51) Int. Cl.[7] ..................... A61K 31/165; C07C 211/27
(52) U.S. Cl. ..................... 514/616; 514/617; 514/625; 564/155; 564/161; 564/192
(58) Field of Search ................ 514/616, 617, 514/625; 564/155, 161, 192

(56) References Cited

U.S. PATENT DOCUMENTS

| 5,484,926 A | 1/1996 | Dressman et al. ........... 546/114 |
| 5,585,397 A | 12/1996 | Tung et al. .................. 514/473 |

OTHER PUBLICATIONS

Jungheim et al.; *Journal of Medicinal Chemistry*, 1996, vol. 39, No. 1, pp. 96–108.
Kaldor et al.; *Journal of Medicinal Chemistry*, 1997, vol. 40, No. 24, pp. 3979–3985.
Branalt et al.; *Tetrahedron Letters*, 1997, vol. 38, No. 19, pp. 3483–3486.
Beaulieu et al.; *J. Org. Chem.*, 1997, vol. 62, No. 11, pp. 3440–3448.
Beaulieu et al.; *Journal of Medicinal Chemistry*, 2000, vol. 43, No. 6, pp. 1094–1108.

*Primary Examiner*—Joseph K. McKane
*Assistant Examiner*—Rebecca Anderson
(74) *Attorney, Agent, or Firm*—Jason D. Ferrone

(57) ABSTRACT

Acylated α-hydroxyarylbutanamines and related sulfonamides, ureas and carbamates that inhibit aspartyl protease are disclosed, as are methods of treating diseases, particularly HIV, using these compounds. The compounds have the formula:

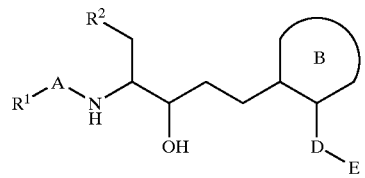

A representative example is:

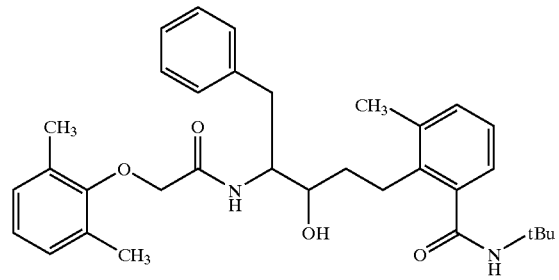

7 Claims, No Drawings

α-HYDROXYARYLBUTANAMINE INHIBITORS OF ASPARTYL PROTEASE

FIELD OF THE INVENTION

The present invention relates to acylated α-hydroxyarylbutanamines and related sulfonamides, ureas and carbamates that inhibit aspartyl protease and to methods of treating diseases using these compounds.

BACKGROUND OF THE INVENTION

The human immunodeficiency virus ("HIV") is the causative agent for acquired immunodeficiency syndrome ("AMDS")—a disease characterized by the destruction of the immune system, particularly of CD4+ T-cells, with attendant susceptibility to opportunistic infections—and its precursor AIDS-related complex ("ARC")—a syndrome characterized by symptoms such as persistent generalized lymphadenopathy, fever and weight loss. As in the case of several other retroviruses, HIV encodes the production of a protease which carries out post-translational cleavage of precursor polypeptides in a process necessary for the formation of infectious virions. A number of synthetic anti-viral agents have been designed to target various stages in the replication cycle of HIV. These agents include compounds which block viral binding to CD4+ T-lymphocytes (for example, soluble CD4), and compounds which interfere with viral replication by inhibiting viral reverse transcriptase (for example, didanosine and zidovudine (AZT)) and inhibit integration of viral DNA into cellular DNA. However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication. The anti-viral potential of HIV protease inhibition has been demonstrated using peptidal inhibitors. Such peptidal compounds, however, are typically large and complex molecules that tend to exhibit poor bioavailability and are not generally efficacious on oral administration. Accordingly, the need still exists for compounds that can effectively inhibit the action of viral proteases, particularly aspartyl proteases, for use as agents for preventing and treating chronic and acute viral infections.

In addition, aspartyl protease inhibitors are of interest for developing antimalarial drugs. Resistance to known antimalarial therapies is becoming an increasing problem, and new therapies are therefore desperately needed. Upon infecting a host, the malaria parasite avidly consumes the host hemoglobin as its source of nutrients. Plasmepsin I and II are proteases from *Plasmodium falciparum* that are necessary during the initial stages of hemoglobin hydrolysis and digestion.

It has been shown that inhibition of plasmepsin by a peptidomimetic inhibitor is effective in preventing malarial hemoglobin degradation and in killing the parasite. Thus, persons skilled in the art expect that plasmepsin inhibitors will provide effective antimalarial therapy.

Another aspartyl protease, cathepsin D, has been implicated in a variety of diseases, including connective tissue disease, muscular dystrophy, and breast cancer. The enzyme is also believed to be the protease which processes the beta-amyloid precursor protein (Dreyer, R. N. et al. Eur. J. Biochem (1994), 244, 265–271 and Ladror, U. S. et al. J. Biol. Chem. (1994), 269, 12422–18428) generating the major component of plaques in the brains of Alzheimer's patients. Consequently, persons of skill in the art expect that inhibitors of cathepsin D will be useful in treating Alzheimer's disease.

Other human aspartyl proteases, such as renin, are involved in the maintenance of blood pressure, and inhibitors of these proteases find use as treatments for hypertension. Inhibitors of aspartyl proteases that process endothelin precursors are similarly useful blocking vasoconstriction.

SUMMARY OF THE INVENTION

It has now been discovered that certain acylated α-hydroxyarylbutanamines and related sulfonamides, ureas and carbamates and pharmaceutically acceptable salts thereof, are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection. The compounds of this invention are capable of inhibiting HIV viral replication in human CD4+ T-cells and are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system. Therefore, in one aspect, the present invention relates to compounds of formula

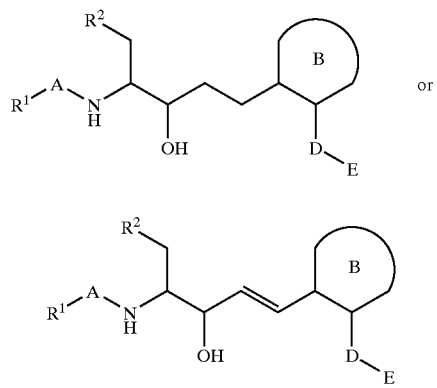

wherein

R$^1$ is chosen from the group consisting of C$_1$–C$_{20}$ alkyl, substituted C$_1$–C$_{20}$ alkyl, aryl, alkylaryl, substituted alkylaryl, C$_3$–C$_{10}$ oxaalkyl, substituted aryl, heterocyclyl, and substituted heterocyclyl;

$R^2$ is chosen from the group consisting of $C_1$–$C_{10}$ hydrocarbon, substituted aryl and heterocyclyl;

A is chosen from the group consisting of —$SO_2$—, —$NHSO_2$—, —$SO_2NHC(O)$—

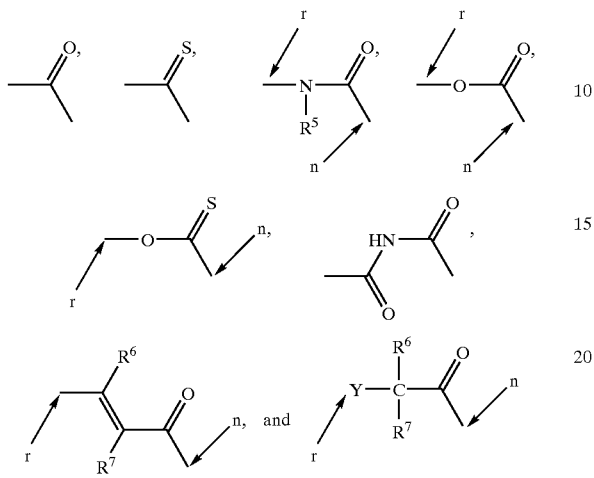

wherein r→designates the point of attachment to $R^1$ and n→designates the point of attachment to N;

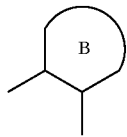

is monocyclic, bicyclic or tricyclic aryl or heteroaryl containing from 0 to 3 substituents chosen from lower alkyl, lower alkoxy, lower alkylthio, hydroxy, mercapto, cyano, carboxy, lower alkoxycarbonyl, (lower alkoxycarbonyl)lower alkoxy, lower alkylaminocarbonyl, amino, lower alkylamino, di(lower alkyl)amino, nitro, halo and haloalkyl;

$R^5$ is chosen from the group consisting of hydrogen, alkyl, aryl and substituted aryl;

$R^6$ and $R^7$ are chosen independently from the group consisting of hydrogen, halogen and lower alkyl;

D is —C(O)— or —NHC(O)—;

E is chosen from the group consisting of $C_5$–$C_8$ alkyl, heterocyclyl, substituted heterocyclyl and $NR^{10}R^{11}$;

$R^{10}$ is hydrogen or lower alkyl;

$R^{11}$ is chosen from $C_1$–$C_{10}$ hydrocarbon, substituted aryl and substituted alkyl; and Y is —O—, —S—, —NH— or a direct bond.

In another aspect, the invention relates to a method of treating or preventing a protease-precipitated disease which comprises administering a therapeutically effective amount of a compound of the formula shown above.

In another aspect, the invention relates to a pharmaceutical composition comprising a pharmaceutically acceptable carrier and a compound of the formula shown above, or a pharmaceutically acceptable salt thereof.

DETAILED DESCRIPTION OF THE INVENTION

The present invention relates to compounds of formulae

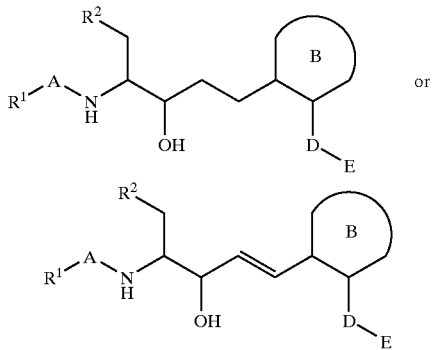

as described above. Preferred subgenera are those in which:

$R^2$ is $C_1$–$C_{10}$ hydrocarbon;

A is chosen from the group consisting of —$SO_2$—,

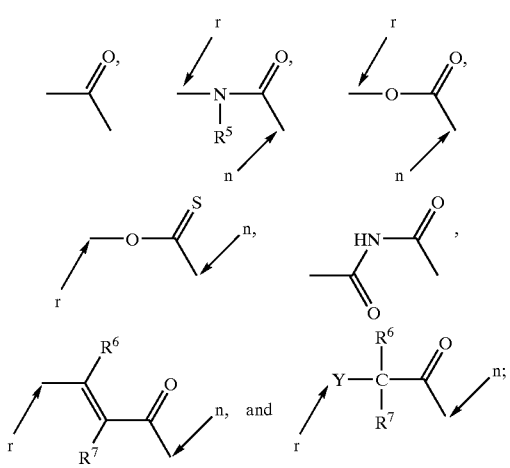

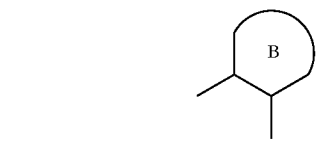

is monocyclic or bicyclic aryl or containing from 0 to 3 substituents chosen from lower alkyl, hydroxy, alkoxy, (lower alkoxycarbonyl)lower alkoxy, nitro and halo;

$R^{10}$ is hydrogen; and $R^{11}$ is chosen from $C_1$–$C_{10}$ hydrocarbon and substituted alkyl.

Particularly preferred subgenera are those in which (1) A is —$SO_2$—;

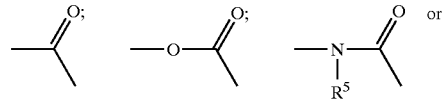

-continued

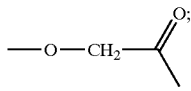

and $R^1$ is chosen from the group consisting of $C_1$–$C_8$ alkyl; phenyl; phenyl substituted with halo, methoxy, hydroxymethyl, allyl, carboxy, trifluoromethyl, anilino, benzoyl, dimethylamino, amino, nitro, cyano, and $C_1$–$C_6$ alkyl; hydroxy $C_1$–$C_6$ alkyl; naphthyl; nitrogenous heterocyclyl; and substituted nitrogenous heterocyclyl;

(2)

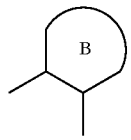

is phenyl, substituted phenyl or naphthyl; most preferably naphthyl or

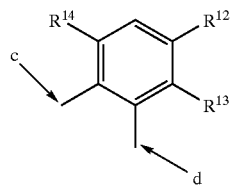

wherein $R^{12}$ is chosen from the group consisting of hydrogen, halogen, lower alkyl, hydroxy, lower alkoxy, nitro and [(lower alkoxy)carbonyl]loweralkoxy;

$R^{13}$ is chosen from the group consisting of hydrogen, halogen, lower alkyl, hydroxy and lower alkoxy;

$R^{14}$ is chosen from the group consisting of hydrogen, halogen, lower alkyl, hydroxy and lower alkoxy;

and wherein c→and d→designate the points of attachment of the carbon chain and D respectively;

(3) D is —NHC(O)— and E is $C_4$–$C_{10}$ hydrocarbon; or D is —C(O)— and E is chosen from the group consisting of:
  (i) nitrogenous heterocyclyl connected to D via N;
  (ii) substituted nitrogenous heterocyclyl connected to D via N; and
  (iii) NHR$^{11}$; wherein
    R$^{11}$ is chosen from $C_4$–$C_{10}$ hydrocarbon and 2-hydroxy-1-phenylethyl.

(4) $R^2$ is phenyl, ethyl, n-propyl or isopropyl.

One representative subgenus is that of formula:

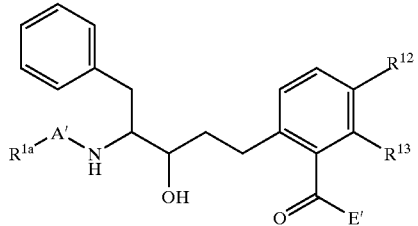

wherein:
  $R^{1a}$ is chosen from the group consisting of $C_1$–$C_{20}$ alkyl, substituted $C_1$–$C_{20}$ alkyl, aryl, alkylaryl, $C_3$–$C_{10}$ oxaalyl, substituted aryl, heterocyclyl, and substituted heterocyclyl;
  A' is chosen from the group consisting of —SO$_2$—,

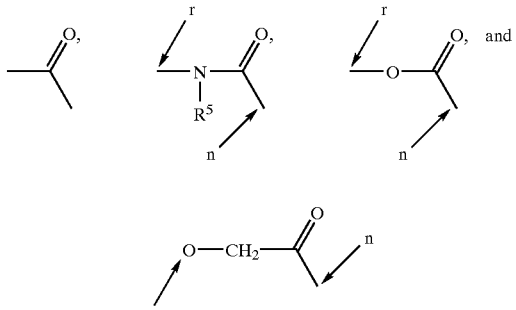

wherein r→designates the point of attachment to $R^1$ and n→designates the point of attachment to N;
  E' is chosen from the group consisting of:
    (i) nitrogenous heterocyclyl connected to D via N;
    (ii) substituted nitrogenous heterocyclyl connected to D via N; and
    (iii) NHR$^1$; and
      R$^{11}$ is chosen from $C_1$–$C_{10}$ hydrocarbon and substituted alkyl;
  $R^{12}$ is chosen from the group consisting of hydrogen, halogen, trifluoromethyl, hydroxy, alkoxy, nitro and [(lower alkoxy)carbonyl]loweralkoxy; and
  $R^{13}$ is chosen from the group consisting of hydrogen, halogen, trifluoromethyl, hydroxy, alkoxy and nitro.

In this subgenus and in related subgenera of the formula

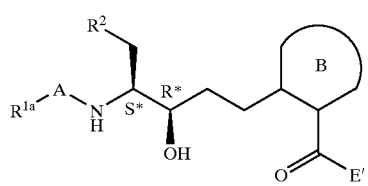

in which $R^2$ is phenyl, ethyl or propyl, the carbon marked S* is preferably of the S configuration and the carbon marked R* is of the R configuration.

Diseases that may be treated or prevented using the compounds of the invention include retroviral infections, malaria, hypertension, connective tissue disease, muscular dystrophy, breast cancer and Alzheimer's disease. These are collectively referred to herein as protease-precipitated diseases.

DEFINITIONS

Throughout this specification the terms and substituents retain their definitions.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ Hydrocarbon includes alkyl, cycloalkyl, alkenyl, alkynyl, aryl and combinations thereof. Examples include phenethyl, cyclohexylmethyl, norhornyl and propargyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Heteroarylalkyl means an alkyl residue attached to a heteroaryl ring. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), chroman, tetrazole, morpholine, thiazole, pyridine, pyridazine, pyrimidine, thiophene, furan, oxazole, oxazoline, isoxazole, dioxane, tetrahydrofuran, thioxanthine, phenothiazine and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, benzooxadiazolyl, triazolyl and tetrahydroquinolinyl.

Substituted alkyl, aryl, cycloalkyl, alkylaryl, heterocyclyl etc. refer to alkyl, aryl, cycloalkyl, or heterocyclyl wherein up to three H atoms in each residue are replaced with loweralkyl; allyl; halogen; haloalkyl; hydroxy; loweralkoxy; hydroxy loweralkyl; carboxy; carboalkoxy (also referred to as alkoxycarbonyl); carboxyalkoxy; carboxamido (also referred to as alkylaminocarbonyl); cyano; formyl; acyl; nitro; amino; alkylamino; dialkylamino; anilino; mercapto; alkylthio; sulfoxide; sulfone; acylamino; amidino; phenyl; benzyl; heteroaryl; phenoxy; benzoyl; benzoyl substituted with amino, hydroxy, methoxy, methyl or halo; benzyloxy and heteroaryloxy. When the base residue contains an alkyl segment, e.g. alkyl or alkylaryl, two hydrogens on the same carbon may be replaced by oxo (=O).

The term "halogen" means fluorine, chlorine, bromine or iodine.

The compounds described herein contain two or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions, John Wiley & Sons 1981. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character, and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". In the case of the present invention, the functionalities that must be protected are most commonly carboxylic acids, amines and alcohols. Suitable groups for that purpose are discussed in standard textbooks in the field of chemistry, such as *Protective Groups in Organic Synthesis* by T. W. Greene [John Wiley & Sons, New York, 1991], which is incorporated herein by reference. The compounds employed as starting materials in the synthesis of the compounds of this invention are well known and, to the extent not commercially available are readily synthesized by standard procedures commonly employed by those of ordinary skill in the art.

ABBREVIATIONS AND DEFINITIONS

The following abbreviations and terms have the indicated meanings throughout:

| | |
|---|---|
| Ac = | acetyl |
| BNB = | 4-bromomethyl-3-nitrobenzoic acid |
| Boc = | t-butyloxy carbonyl |

-continued

| | |
|---|---|
| Bu = | butyl |
| c- = | cyclo |
| DBU = | diazabicyclo[5.4.0]undec-7-ene |
| DCM = | dichloromethane = methylene chloride = $CH_2Cl_2$ |
| DEAD = | diethyl azodicarboxylate |
| DIBAL = | diisobutylaluminum hydride |
| DIC = | diisopropylcarbodiimide |
| DIEA = | N,N-diisopropylethyl amine |
| DMAP = | 4-N,N-dimethylaminopyridine |
| DMF = | N,N-dimethylformamide |
| DMSO = | dimethyl sulfoxide |
| DVB = | 1,4-divinylbenzene |
| EEDQ = | 2-ethoxy-1-ethoxycarbonyl-1,2-dihydroquinoline |
| Et = | ethyl |
| Fmoc = | 9-fluorenylmethoxycarbonyl |
| GC = | gas chromatography |
| HATU = | O-(7-Azabenzotriazol-1-yl)-1,1,3,3-tetramethyluronium hexafluorophosphate |
| HOAc = | acetic acid |
| HOBt = | hydroxybenzotriazole |
| Me = | methyl |
| mesyl = | methanesulfonyl |
| MTBE = | methyl t-butyl ether |
| NMM = | N-methylmorpholine |
| NMO = | N-methylmorpholine oxide |
| PEG = | polyethylene glycol |
| Ph or φ = | phenyl |
| PhOH = | phenol |
| PfP = | pentafluorophenol |
| PPTS = | pyridinium p-toluenesulfonate |
| PyBroP = | bromo-tris-pyrrolidino-phosphonium hexafluorophosphate |
| rt = | room temperature |
| sat'd = | saturated |
| s- = | secondary |
| t- = | tertiary |
| TBDMS = | t-butyldimethylsilyl |
| TFA = | trifluoroacetic acid |
| THF = | tetrahydrofuran |
| TMOF = | trimethyl orthoformate |
| TMS = | trimethylsilyl |
| tosyl = | p-toluenesulfonyl |
| Trt = | triphenylmethyl |

The pharmaceutically acceptable salts of the invention are typically formed by reacting a compound such as 000971 or 001035 (in Table 1 below) with an equimolar or excess amount of acid or base respectively. The reactants are generally combined in a mutual solvent such as diethyl ether or toluene, for acid addition salts, or water or alcohols for base addition salts, and the salts normally precipitate out of solution within about one hour to about ten days and can be isolated by filtration or other conventional methods. In addition, some of the compounds may form solvates with water or with common organic solvents, and such solvates are included within the scope of the compounds of the present invention.

Scheme I details a method for the production of compound 9, which is a typical subgenus of compounds of the invention. The tables, which follow the scheme, illustrate many compounds that can be synthesized according to Scheme I, but Scheme I is not limited by the compounds in the tables nor by any particular substituents employed in the schemes for illustrative purposes. The examples illustrate the application of the synthesis described in Scheme I to specific compounds.

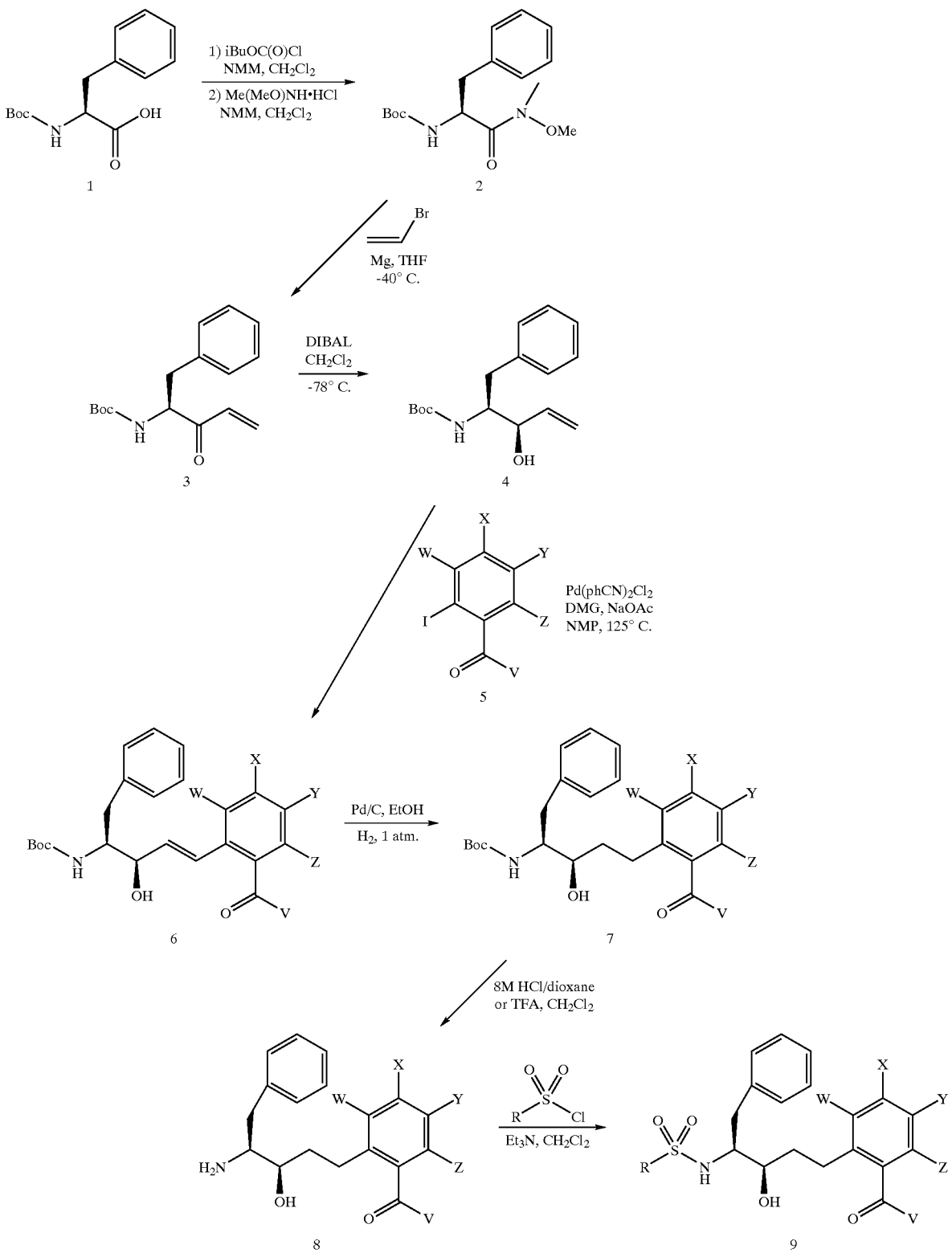

Scheme I

For illustrative purposes preparation of sulfonamide 9 via reaction with the sulfonyl chloride is shown, however, one skilled in the art will appreciate that amides, thioamides, ureas, sulfonamides, carbamates, sulfamides and similar structures can also be obtained in analogous reactions using standard conditions. For example, the free amine 8 can be reacted with isocyanates in a solvent such as $CH_2Cl_2$ in the presence a base such a N-methylmorpholine to generate urea structures, or a carbamate group can be formed by the treatment of 8 with a carbamyl chloride or azide under similar conditions. Also standard amide coupling techniques can be used to form an amide group at the free amine. Techniques for these procedures are well known to those skilled in the art. The thioamides may be prepared by treatment of the amide with Lawesson's reagent. One skilled in the art will appreciate that compounds 5 can be prepared in a like manner from the appropriate 2-iodobenzoic acid.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the compounds of the present invention are excellent ligands for aspartyl proteases, particularly HV-1 and HIV-2 proteases, although renin, endothelin, cathepsin D and plasmepsin may also be inhibited. As protease inhibitors, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. A further embodiment of the present invention is a method of treating HIV infection, or inhibiting HIV replication, comprising administering to a mammal in need of treatment an HIV inhibiting dose of a compound of the invention or a pharmaceutically acceptable salt or solvate thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "effective amount" as used herein, means an amount of a compound of the present invention which is capable of inhibiting the HIV protease mediated viral component production and assembly. The HIV protease inhibition contemplated by the present method includes both therapeutic and prophylactic treatment, as appropriate. Methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection. Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect. individuals over an extended period time against HIV infection. As such, the protease inhibitors of this invention can be administered as agents for treating or preventing HIV infection in a mammal.

The term "pro-drug" as used herein refers to pharmacologically acceptable derivatives, for example, but not limited to, esters and amides, such that the resulting biotransformation product of the derivative is the active drug. Pro-drugs are known in the art and are described generally in, e.g., Goodman and Gilman's "Biotransformation of Drugs," in the Pharmacological Basis of Therapeutics, 8th Ed., McGraw Hill, Int. Ed. 1992, page 13–15, which is hereby incorporated by reference in its entirety.

The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.01 mg/kg to about 50 mg/kg of body weight of an active compound of this invention. Preferred daily doses generally will be from about 0.05 mg/kg to about 20 mg/kg and ideally less than 10 mg/kg.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. AntiHIV agents targeting such early life cycle events include, didanosine (ddI), alcitabine (ddC), d4T, zidovudine (AZT), polysulfated polysaccharides, sT4 (soluble CD4), ganiclovir, dideoxycytidine, trisodium phosphonofonnate, eflornithine, ribavirin, acyclovir, alpha interferon and trimenotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral integrase. Combination therapies according to this invention exert a synergistic effect in inhibiting HIV replication because each component agent of the combination acts on a different site of HIV replication. The use of such combinations also advantageously reduces the dosage of a given conventional antiretroviral agent which would be required for a desired therapeutic or prophylactic effect as compared to when that agent is administered as a monotherapy. Combinations may reduce side effects while maintaining anti-retroviral activity, or they may increase efficacy without increasing toxicity. Combinations also reduce potential of resistance to single agent therapies, while minimizing any associated toxicity.

In particular, we have discovered that these compounds act synergistically in preventing the replication of HIV in human T cells. Preferred combination therapies include the administration of a compound of this, invention with AZT, ddI, ddC or d4T. Alternatively, the compounds of this invention may also be co-administered with other HIV protease inhibitors such as Ro 31-8959 (Roche), L-735,524 (Merck), XM 323 (Du-Pont Merck) and A-80,987 (Abbott) to increase the effect of therapy or prophylaxis against various viral mutants or members of other HIV quasi species.

Particularly preferred classes of agents for use in combination with the inventive compounds include other antiviral agents such as other protease inhibitors and reverse transcriptase inhibitors of the nucleoside, non-nucleoside, or nucleotide analog variety. Other preferred classes of antiviral agents include fusion inhibitors, zinc finger inhibitors, integrase inhibitors, cellular inhibitors, and molecules that block HIV receptors such as the CD4, CCR5, CXCR4 receptors, etc. Many of the preferred combinations include at least three agents. For example, certain preferred combinations will include one or more compounds of the present invention together with one or more other protease inhibitors together with one or more reverse transcriptase inhibitors.

Particularly preferred retroviral protease inhibitors include those currently approved by the FDA such as saquinavir, ritonavir, indinavir, nelfinavir, and amprenavir and investigational agents such as tipranivir (PNU-140690), lopinavir (ABT-378), BMS-234475, DMP-450, L-756,423, AG1776, and PD-178390. Preferred reverse transcriptase inhibitors include the FDA-approved NRTIs zidovudine (ZDV,AZT), didanosine (dideoxyinosine, ddI), zalcitabine (dideoxycytidine; ddC), stavudine (d4T), lamivudine (3TC), and abacarir (ABC), the investigational NRTIs emtricitabine (FFC), dOTC, and dAPD, the FDA-approved NNRTIs nevirapine (NVP), delavirdine (DLV), and efavirenz (EFZ), the investigational NNRTIs emivirine, (MKC442), capravirine (AG 1549), DMP/DPC 961, DMP/DPC 963), calanolide A, GW420967X, and PNU142721, and the nucleotide analogs adefovir (ADV) and tenofovir. Other preferred agents include fusion inhibitors such as T-20, peptide 2, T-1249, AMD-3100, PRO 542, FP-21399, rCD4/CD4-OgG, and CD4-PE40, zinc finger inhibitors such as ADA, cellular inhibitors such as hydroxyurea (HU), peldesine (Bcx-34), and topotecan.

Additional agents of potential utility in combination with the inventive compounds include the protease inhibitor Ro 31-8959, SC-52151, KNI-227, KNI-272 and the like, reverse transcriptase inhibitors such as R82193, L-697,661, HEPT compounds, L,697,639, R-82150, U-87201E and the like, Bch-189, AzdU, carbovir, DDA, D4C, DP-AZT,FLT (fluorothyrnidine), BCG-189, 5-halo-3'-thiadideoxycytidine, PMEA, TAT inhibitors (for example, RO-24-7429 and the like). AL-721, polymannoacetate, trisodium phosphonoformate, HPA-23, eflonithine, Peptide T, Reticulose (nucleophosphoprotein), ansamycin LM 427, trimetrexate, UA001, ribavirin, oxetanocin, oxetanocin-G, cylobut-G, cyclobut-A, ara-M, BW882C87, oscarnet, BW256U87, BW348U87, L69,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, butyl-DNJ, hypericin, oxamyristic acid, dextran sulfate and pentosan polysulfate.

Immunomodulators that can be administered in combination with a compound of the present invention include bropirimine, Ampligen, anti-human alpha interferon antibody, CL246,738, Imreg-1, Imreg-2, diethydithiocarbamate, interleukin-2, interleukin-3, interleukin-4, alpha interferon, beta interferon, gamma interferon, inosine pranobex, methionine enkephalin, muramyl-tripeptide, TP-5, erythropoietin, naltrexone, tumor necrosis factor, FK-565, FK-506, GM-CSF, alpha interferon immunoglobulin, IGP-1, anti-leu-3A, isopinosine, IVG, and HIVIG. Certain techniques for immunomodulation, such as autologous CD8+infusion, autovaccination, biostimulation, extracorporeal photophoresis, hyperthermia, passive immunotherapy and polio vaccine hyperimmunization may also be used with the compounds of the invention.

Any of a variety of HIV or AIDS vaccines, for example gp120(recombinant), Env2-3 (gp120), HGP-30, HIV-Immunogen, p24 (recombinant) and VaxSyn HIV-1 (p24), can be used in combination with a compound of the present invention. We prefer administering the compounds of this invention as single agents or in combination with retroviral reverse transcriptase inhibitors, such as derivatives of AZT, or other HIV aspartyl protease inhibitors. The compounds of this invention can also be administered in combination with antibiotics (e.g., pentamidine isethiorate) to prevent or combat infection and disease associated with HIV infections, such as AIDS and ARC.

When the compounds of this invention are administered in combination therapies with other agents, they may be administered as separate dosage forms administered sequentially or concurrently to the patient. Alternatively, pharmaceutical or prophylactic compositions according to this invention may combine an aspartyl protease inhibitor of this invention and another therapeutic or prophylactic agent in a single dosage form.

Although this invention focuses on the use of the compounds disclosed herein for preventing and treating HIV infection, the compounds can also be used as inhibitory agents for other viruses which depend on similar aspartyl proteases for obligatory events in their life cycle. These viruses include other retroviruses, such as simian immunodeficiency viruses, HTLV-I and HTLV-II.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerLdes. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 50 mg/kg body weight per day and ideally from about 0.1 to about 10 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms. As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. These and other uses which characterize commercial aspartyl protease inhibitors will be evident to those of ordinary skill in the art.

Many compounds of this invention are illustrated in Tables 1–4 which follow. The inhibition constants of compounds are indicated as "A" when the $IC_{50}$ is less than 0.1 $\mu M$, "B" when the $IC_{50}$ is between 0.1 $\mu M$ and 10 $\mu M$, and "C" when the $IC_{50}$ is greater than 10 $\mu M$. In the exemplary compounds in the tables that follow, the carbon bearing the α-hydroxyl is of the R absolute configuration and the adjacent carbon bearing the amine is of the S absolute configuration.

TABLE 1
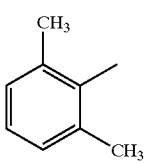
| Example | R¹ | A | R¹² | R¹³ | R¹¹ | IC$_{50}$ in μM |
|---|---|---|---|---|---|---|
| 001237 | 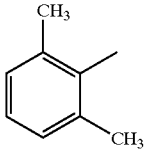 | —OCH$_2$C(O) | CH$_3$ | H | t-Bu | A |
| 000987 | 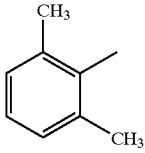 | —OCH$_2$C(O) | H | H | t-Bu | A |
| 001239 | 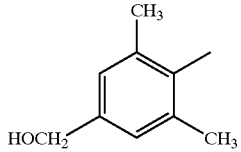 | —OCH$_2$C(O) | H | F | t-Bu | A |
| 001267 | 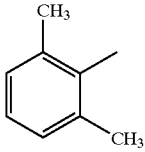 | —OCH$_2$C(O) | H | H | t-Bu | A |
| 001249 | 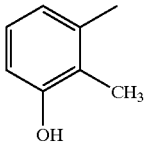 | —OCH$_2$C(O) | H | CH$_3$ | t-Bu | A |
| 000972 | 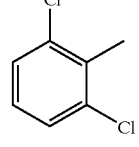 | —C(O)— | H | H | t-Bu | A |
| 000970 |  | —C(O)— | H | H | t-Bu | A |

TABLE 1-continued
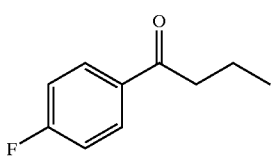
| Example | R¹ | A | R$^{12}$ | R$^{13}$ | R$^{11}$ | IC$_{50}$ in μM |
|---|---|---|---|---|---|---|
| 000973 | 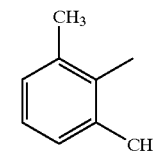 | —C(O)— | H | H | t-Bu | A |
| 000951 | 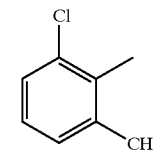 | —C(O)— | H | H | t-Bu | A |
| 001215 | 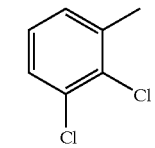 | —OCH$_2$C(O)— | H | H | t-Bu | A |
| 000955 |  | —C(O)— | H | H | t-Bu | A |
| 000180 | 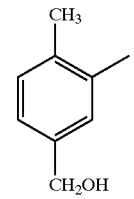 | —OC(O)— | H | H | t-Bu | A |
| 000895 | 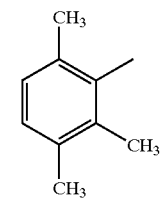 | —C(O)— | H | H | t-Bu | A |
| 001201 |  | —OCH$_2$C(O)— | H | H | t-Bu | A |

TABLE 1-continued
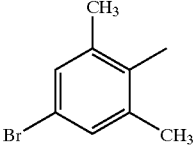
| Example | R¹ | A | R¹² | R¹³ | R¹¹ | IC$_{50}$ in μM |
|---|---|---|---|---|---|---|
| 001218 | 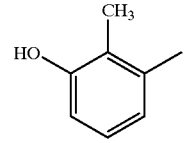 | —OCH$_2$C(O)— | H | H | t-Bu | A |
| 000776 | t-Bu | —OCH$_2$C(O)— | H | H | t-Bu | A |
| 000373 | Et | —OCH$_2$C(O)— | H | H | t-Bu | A |
| 001246 | 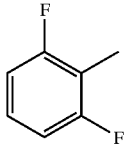 | —OCH$_2$C(O)— | H | H | t-Bu | A |
| 001214 | 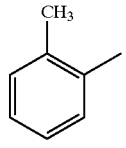 | —OCH$_2$C(O)— | H | H | t-Bu | A |
| 001173 | 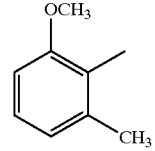 | —OCH$_2$C(O)— | H | H | t-Bu | A |
| 001213 | 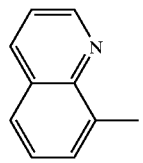 | —OCH$_2$C(O)— | H | H | t-Bu | A |
| 000156 | t-Bu | —OC(O)— | H | H | i-Bu | A |
| 000245 | phenyl | —C(O)— | H | H | t-Bu | B |
| 00878 | 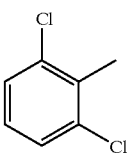 | —SO$_2$— | H | H | t-Bu | B |
| 001203 |  | —OCH$_2$C(O)— | H | H | t-Bu | B |

TABLE 1-continued
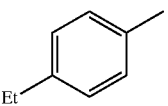
| Example | R¹ | A | R¹² | R¹³ | R¹¹ | IC$_{50}$ in μM |
|---|---|---|---|---|---|---|
| 000874 | 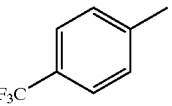 | —SO$_2$— | H | H | t-Bu | B |
| 000877 | 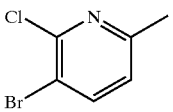 | —SO$_2$— | H | H | t-Bu | B |
| 000879 | 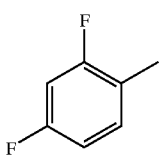 | —SO$_2$— | H | H | t-Bu | B |
| 000901 | 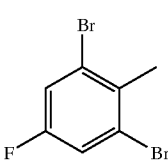 | —C(O)— | H | H | t-Bu | B |
| 001226 | 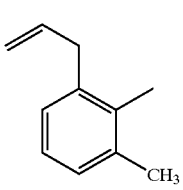 | —OCH$_2$C(O)— | H | H | t-Bu | B |
| 001206 |  | —OCH$_2$C(O)— | H | H | t-Bu | B |
| 000969 | 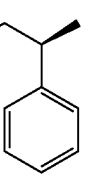 | —C(O)— | H | H | t-Bu | B |
| 000244 | phenyl | —OCH$_2$C(O)— | H | H | t-Bu | B |
| 001054 | t-Bu | —OC(O)— | H | H |  | B |

TABLE 1-continued
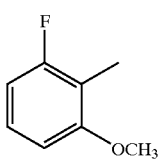
| Example | R¹ | A | R¹² | R¹³ | R¹¹ | IC$_{50}$ in μM |
|---|---|---|---|---|---|---|
| 001217 | 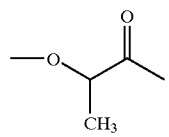 | —OCH$_2$C(O)— | H | H | t-Bu | B |
| 000243 | phenyl | 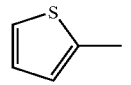 | H | H | t-Bu | B |
| 000880 | 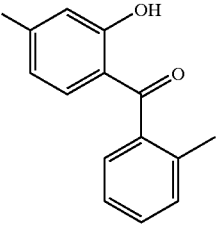 | —SO$_2$— | H | H | t-Bu | B |
| 001034 | 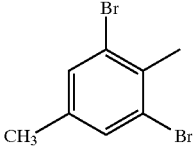 | —C(O)— | H | H | t-Bu | B |
| 001225 | 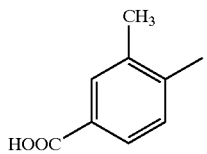 | —OCH$_2$C(O)— | H | H | t-Bu | B |
| 000344 | t-Bu | —OC(O)— | H | H | n-Bu | B |
| 001279 | 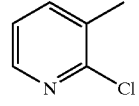 | —OCH$_2$C(O)— | H | H | t-Bu | B |
| 001268 |  | —OCH$_2$C(O)— | H | H | t-Bu | B |
| 000891 | n-Bu | —NHC(O)— | H | H | t-Bu | B |

TABLE 1-continued

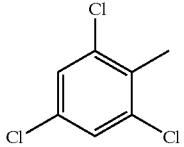

| Example | R¹ | A | R¹² | R¹³ | R¹¹ | IC$_{50}$ in μM |
|---|---|---|---|---|---|---|
| 001224 | 2,4,6-trichloro-3-methylphenyl | —OCH$_2$C(O)— | H | H | t-Bu | A |
| 000881 | i-Pr | —SO$_2$— | H | H | t-Bu | B |
| 001006 | phenyl | —N(φ)C(O)— | H | H | t-Bu | B |
| 000766 | t-Bu | —OC(O)— | H | H | isopentyl | B |
| 000770 | Et | —OC(O)— | H | H | isopentyl | B |
| 001186 | 2,5-dimethylphenyl | —OCH$_2$C(O)— | H | H | t-Bu | B |
| 001047 | 4-benzoylphenyl | —C(O)— | H | H | t-Bu | B |
| 000771 | Et | —NHC(O)— | H | H | t-Bu | B |
| 000763 | φCH$_2$CH$_2$ | —C(O)— | H | H | t-Bu | B |
| 001053 | t-Bu | —OC(O)— | H | H | (R)-2-hydroxy-1-phenylethyl | B |
| 000242 | (S)-1-hydroxyethyl | —C(O)— | H | H | t-Bu | B |
| 001008 | 4-methylmorpholinyl | —C(O)— | H | H | t-Bu | B |
| 001154 | 3,4-dimethylisoxazol-5-yl | —C(O)— | H | H | t-Bu | B |

TABLE 1-continued
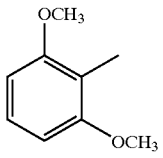
| Example | R¹ | A | R¹² | R¹³ | R¹¹ | IC$_{50}$ in μM |
|---|---|---|---|---|---|---|
| 000966 | 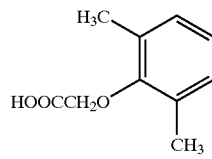 | —C(O)— | H | H | t-Bu | B |
| 001278 | 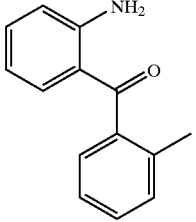 | —C(O)— | H | H | t-Bu | B |
| 001040 | 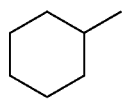 | —C(O)— | H | H | t-Bu | B |
| 001228 | 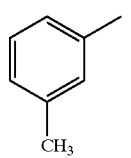 | —OCH$_2$C(O)— | H | H | t-Bu | B |
| 001185 | 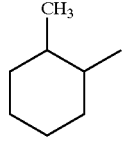 | —OCH$_2$C(O)— | H | H | t-Bu | B |
| 00762 | benzyl | —C(O)— | H | H | t-Bu | B |
| 001229 | 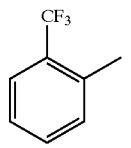 | —OCH$_2$C(O)— | H | H | t-Bu | B |
| 001204 |  | —OCH$_2$C(O)— | H | H | t-Bu | B |
| 001190 | phenyl | —SCH$_2$C(O)— | H | H | t-Bu | B |

TABLE 1-continued
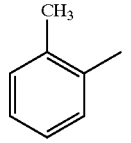
| Example | R¹ | A | R¹² | R¹³ | R¹¹ | IC$_{50}$ in μM |
|---|---|---|---|---|---|---|
| 001014 | 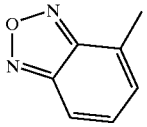 | SO$_2$NHC(O)— | H | H | t-Bu | B |
| 001012 | 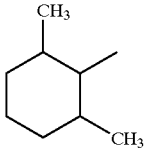 | —SO$_2$— | H | H | t-Bu | B |
| 001230 | 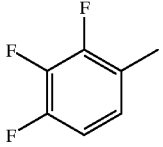 | —OCH$_2$C(O)— | H | H | t-Bu | B |
| 001227 | 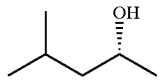 | —OCH$_2$C(O)— | H | H | t-Bu | B |
| 001231 | (CH$_3$CH$_2$)$_2$CH— | —OCH$_2$C(O)— | H | H | t-Bu | B |
| 001192 | phenyl | —NHCH$_2$C(O)— | H | H | t-Bu | B |
| 001219 | 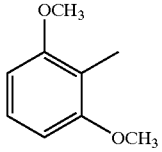 | —C(O)— | H | H | t-Bu | B |
| 001210 |  | —OCH$_2$C(O)— | H | H | t-Bu | B |
| 000760 |  | —OCH$_2$C(O)— | H | H | t-Bu | B |

TABLE 1-continued
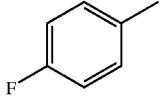
| Example | R¹ | A | R¹² | R¹³ | R¹¹ | IC$_{50}$ in μM |
|---|---|---|---|---|---|---|
| 001017 | 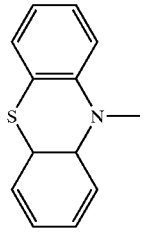 | —OC(S)— | H | H | t-Bu | C |
| 000964 | t-Bu | —OC(O)— | OH | H | t-Bu | C |
| 00241 | 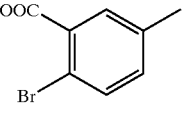 | —C(O)— | H | H | t-Bu | C |
| 001035 | 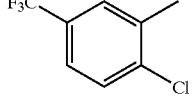 | —C(O)— | H | H | t-Bu | B |
| 001036 | 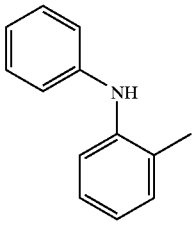 | —C(O)— | H | H | t-Bu | C |
| 001020 | 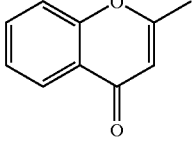 | —C(O)— | H | H | t-Bu | C |
| 000974 | 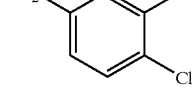 | —C(O)— | H | H | t-Bu | C |
| 000971 |  | —C(O)— | H | H | t-Bu | B |

TABLE 1-continued

[Structure: phenyl-CH2-CH(NH-A-R1)-CH(OH)-CH2-CH2-aryl(R12, R13)-C(O)NHR11]

| Example | R¹ | A | R¹² | R¹³ | R¹¹ | IC₅₀ in μM |
|---------|----|----|-----|-----|-----|-----------|
| 00968 | 2-benzoylphenyl | —C(O)— | H | H | t-Bu | B |
| 000967 | 3,5-dichlorophenyl | —C(O)— | H | H | t-Bu | B |
| 001202 | 2,4,6-trimethylphenyl | —C(O)— | H | H | t-Bu | A |
| 000954 | 4-(dimethylamino)phenyl | —C(O)— | H | H | t-Bu | C |
| 000950 | 4-methylphenyl | —C(O)CH=CHC(O)— | H | H | t-Bu | C |
| 001211 | 2,6-dimethyl-4-nitrophenyl | —OCH₂C(O)— | H | H | t-Bu | B |
| 001182 | 3,5-difluorophenyl | —OCH₂C(O)— | H | H | t-Bu | C |

TABLE 1-continued
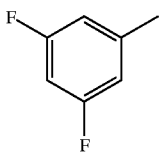
| Example | R¹ | A | R¹² | R¹³ | R¹¹ | IC$_{50}$ in μM |
|---|---|---|---|---|---|---|
| 000948 | 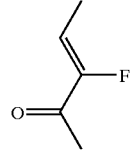 | —C(O)— | H | H | t-Bu | C |
| 000947 | phenyl | 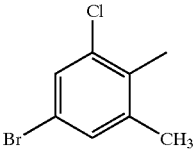 | H | H | t-Bu | C |
| 001216 |  | —OCH$_2$C(O)— | H | H | t-Bu | B |
| 000946 | 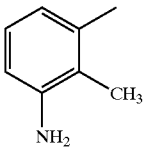 | —C(O)— | H | H | t-Bu | C |
| 000945 | 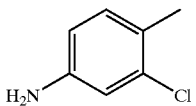 | —C(O)— | H | H | t-Bu | C |
| 000944 | 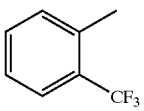 | —C(O)— | H | H | t-Bu | C |
| 001042 |  | —C(O)— | H | H | t-Bu | B |

TABLE 1-continued
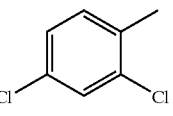
| Example | R¹ | A | R¹² | R¹³ | R¹¹ | IC$_{50}$ in μM |
|---|---|---|---|---|---|---|
| 000902 | 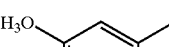 | —C(O)— | H | H | t-Bu | B |
| 000900 | 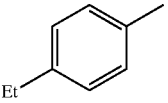 | —C(O)— | H | H | t-Bu | B |
| 000893 | 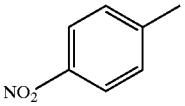 | —NHC(O)— | H | H | t-Bu | B |
| 000892 | iPr | —NHC(O)— | H | H | t-Bu | B |
| 000890 | n-pentyl | —NHC(O)— | H | H | t-Bu | B |
| 000889 | 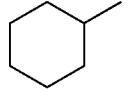 | —NHC(O)— | H | H | t-Bu | B |
| 000882 | 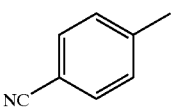 | —NHC(O)— | H | H | t-Bu | C |
| 000876 | 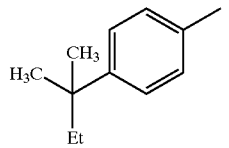 | —SO$_2$— | H | H | t-Bu | B |
| 000875 | 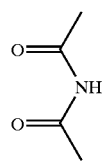 | —SO$_2$— | H | H | t-Bu | B |
| 000869 | ClCH$_2$ | 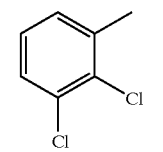 | H | H | t-Bu | C |
| 001010 |  | —SO$_2$— | H | H | t-Bu | C |

TABLE 2
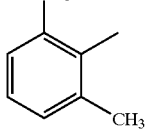
| Example | R¹ | A | R¹² | R¹³ | R¹⁴ | IC₅₀ in μM |
|---|---|---|---|---|---|---|
| 001232 | CH₃ (2,3-dimethylphenyl) | —OCH₂C(O)— | CH₃ | H | H | B |
| 001233 | CH₃ (2,3-dimethylphenyl) | —OCH₂C(O)— | H | H | CH₃ | A |
| 001248 | CH₃ (2,3-dimethylphenyl) | —OCH₂C(O)— | H | CH₃ | H | A |
| 000207 | EtO | —C(O)— | H | H | H | B |
| 001234 | CH₃ (2,3-dimethylphenyl) | —OCH₂C(O)— | H | F | H | B |
| 001048 | t-Bu | —OC(O)— | NO₂ | H | H | B |
TABLE 3
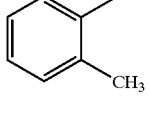
| Example | R¹ | Q | IC₅₀ in μM |
|---|---|---|---|
| 000857 | EtO | —CH₂CH₂— | B |
| 000849 | t-Bu | —CH₂CH₂— | B |
| 000848 | t-Bu | —CH=CH— | B |
TABLE 4
Miscellaneous Compounds
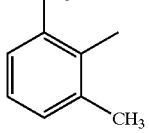
001238    IC₅₀ = A
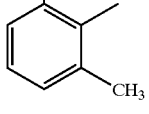
001294    IC₅₀ = C
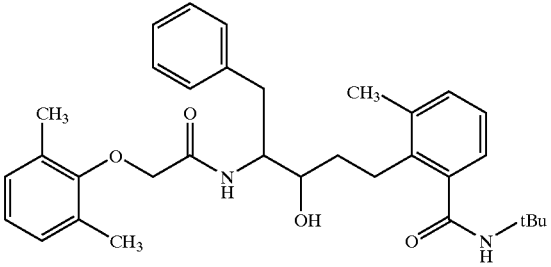
000765    IC₅₀ = B
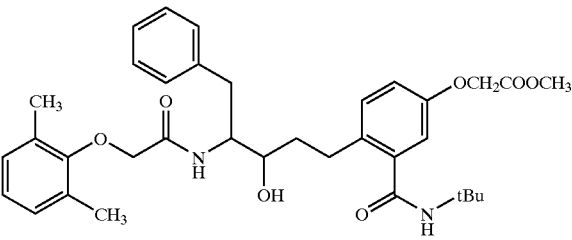
000769 IC₅₀ = B

TABLE 4-continued

Miscellaneous Compounds

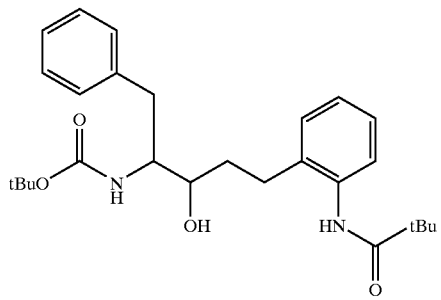

000774   IC$_{50}$ = B

The following Preparations and Examples further illustrate the compounds of the present invention and methods for their synthesis. The examples are not intended to be limiting to the scope of the invention in any respect and should not be so construed.

GENERAL MATERIALS AND METHODS

Unless otherwise noted, NMR data appearing in the examples refers to the free base of the subject compound. In the following Preparations and Examples, the terms melting point, nuclear magnetic resonance spectra, electrospray mass spectra, infrared spectra, ultraviolet spectra, elemental analysis, specific rotation, high performance liquid chromatography, and thin layer chromatography are abbreviated m.p., n.m.r, m.s., i.r., u.v., anal., o.r., HPLC, and TLC, respectively. In addition, the absorption maxima listed for the i.r. spectra are only those of interest and not all of the maxima observed.

In conjunction with n.m.r. spectra, the following abbreviations are used: "s" is singlet, "d" is doublet, "dd" is doublet of doublets, "t" is triplet, "q" is quartet, "m" is multiplet. The n.m.r. spectra were obtained on a Varian Associates Inova 400 400 MHz instrument. The chemical shifts are expressed in delta values (parts per million downfield from tetramethylsilane). The mass spectra were taken on a Micromass LCT using an electrospray ionization source.

Thin layer chromatography (LC) was carried out using 0.25 mm thick E. Merck silica gel 60 F254 plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 F254 plates ("prep plates") of 0.5, 1.0, or 2.0 mm thickness. Following development of the plate, the band of silica containing the desired compound was isolated and eluted with an appropriate solvent. Melting points are uncorrected.

Phenoxy acetic acid derivatives were prepared using the procedure described essentially by P. L. Beaulieu et al., *J. Med Chem.* 43, 1094, (2000). The preparation of (2,6-difluoro-phenoxy)-acetic acid was given as an example. (S)-[1-(Methoxymethylcarbamoyl)-2-phenylethyl]carbamic acid tert-butyl ester In a dry round bottom flash under nitrogen 50 g (0.188 mol) of Boc phenylalanine was dissolved in 500 mL of methylene chloride and 25 mL (0.228 mol) of N-methyl-morpholine was added. The reaction was cooled to −20° C. and isobutylchloroformate (23.3 mL, 0.180 mol) was added drop wise. The reaction was warmed to 0° C. and allowed to stir for 30 min. In a separate flask 15.8 g (0.189 mol) of Dimethylhydroxylamine HCl was dissolved in 100 mL of DMF and 300 mL of methylene chloride was added followed by 25 mL (0.228 mol) of N-methyl-morpholine. The mixture was allowed to stir for 30 min. and the white HCl salt of N-methyl morpholine precipitates after ~30 sec. After the appropriate time, the amine was added via cannula to the Boc phenylalanine mixed anhydride at 0° C. After all the liquid has been transferred, the solids are poured into the reaction vessel with the aid of 50 ml of dry methylene chloride. The reaction was allowed to warm to room temperature over 3 h. and then poured into 200 mL of 1 N HCl. The layers were separated and the aqueous layer was washed with three 200 mL portions of methylene chloride. The combined organics were dried over Na$_2$CO$_3$ and then condensed in vacuo. The resulting residue containing DMF was re dissolved in Ethyl acetate 800 mL and washed with two 200 mL portions of 1 N HCl, two 200 mL portions of saturated NaHCO$_3$,200 mL of water and 200 mL of brine. The organic layer was then dried over Na$_2$CO$_3$ and condensed in vacuo to give 56.3 g (97%) of a yellowish viscous oil, which was used without further purification.

((S)-1-Benzyl-2-oxo-but-3-enyl)-carbamic Acid Tert-butyl Ester

In a dry round bottom flash under nitrogen 12 g (0.50 mol) of magnesium powder was slum ed in 10 mL of dry THF then 418 mL (0.418 mol) of vinyl bromide (1M in THF) was added at such a rate as to maintain a gentle boil. After the bromide has been added (~1 h) the reaction was stirred a further 30 min. Meanwhile in a separate flask 51.5 g (0.167 mol) of the Weinreb amide was dissolved in 500 mL of THF in a second dry round bottom flask and cooled to 0° C. in an ice bath. The vinyl Grignard was added via cannula and the reaction was allowed to stir at 0° C. for 3 hours and at room temperature for 20 hours. After the reaction was complete it was poured slowly into a mixture of 2 N HCl (500 mL) and ice 200 g (gas evolution!). The quench was maintained strongly acidic through out and excess HCl was added if needed. The mixture was transferred to a seperatory funnel and the layers are separated. The aqueous layer was washed with three 200 mL portions of ethyl acetate and the combined organics are dried over Na$_2$SO$_4$. The solvent was removed to a volume of 100 mL and 500 mL of hexane was added. The solution was treated with 5 g of charcoal and passed through a 100×70 cm plug of silica using 10% ethyl acetate in hexanes (300 mL) as an eluant. The resulting light yellow material was cooled overnight and the white crystals which form are collected by vacuum filtration and washed with cold (−20° C.) hexanes to give 21.6 g of product. A further 14.6 g of product can be obtained by concentrating the mother liquor dissolving the resulting yellow oil in 10% ethyl acetate in hexanes (100 mL) and passing through a second silica gel plug using 10% ethyl acetate in hexanes (300 mL) as an eluant. The resulting white solid was obtained in 78% yield and used without further purification Yield=36.2 g (78%) 1H NMR 7.22 (m, 2H); 7.07 (d, J=6.8, 2H); 6.35 (m, 2H); 5.80 (dd, J=10, 1.6, 1H); 5.17 (br d, J=6.8, 1H); 4.82 (q, J=7.2, 1H); 3.10 (dd, J=−14, 6.4, 1H); 2.94 (d, J=14, 5.2, 1H); 1.38 (s, 9H)

((1S,2R)-1-benzyl-2-hydroxybut-3-enyl)carbamic Acid tert-butyl Ester

In a dry round bottom flask under nitrogen 39 g (0.141 mol) of the enone was dissolved in 700 mL of dry methylene chloride and cooled to −78° C. DIBAL (212 mL, 0.212 mol) was added at a rate of 20 mL/h. Care was taken not to allow the internal temperature to rise above −60° C. After addition was complete the reaction was followed by TLC (SiO$_2$, 30% ethyl acetate in hexanes) and was complete in 2 h at −78° C. The excess DIBAL was quenched by addition of isopropanol (5 mL) at −78° C. and the reaction was allowed to warm to 0° C. at which point it was poured into 1L of 1 N Rochelle's salt and allowed to stir overnight. The layers are separated and the aqueous phase was extracted with two 200 mL portions of methylene chloride. The combined organics are washed with 300 mL of brine and dried over Na$_2$SO$_4$. The solvent was removed in vacuo and the resulting sticky white solid was recrystallized from Et$_2$O and hexanes to give 26.2 g (67%) of the product. 1H NMR: 7.15 (m5H); 5.11 (br s, 1H); 4.88 (br s, 1H); 3.62 (s, 3H); 3.18 (s, 3H); 2.98 (m, 2H); 2.81 (m, 2H); 1.38 (s, 9H).

(2,6-Difluoro-phenoxy)-acetic Acid 2,6-Difluoro-phenol (10.0 g, 92.47 mmol) was dissolved in 15.0 mL of acetone, K$_2$CO$_3$ (7.40 g, 92.47 mmol) and α-bromoacetate (15.44 g, 10.25 mL, 231.18 mmol) were added and the reaction was allowed to reflux overnight. The mixture was filtered through a plug of cotton and the solvent removed in vacuo to give 18.93 g as a colorless oil, 98% yield. $^1$H NMR (400 MHz, CDCl$_3$): σ 1.26 (t, J=m Hz, 3H), 2.29 (s, 3H), 4.24 (q, J=Hz, 2H), 4.61 (s, 2H), 6.64 (d, J=Hz, 1H), 6.83 (t, J=Hz, 1H), 7.16 (q, J=Hz, 2H) $^{13}$C NMR (CDCl$_3$): 169.37, 156.36, 131.13, 127.51, 126.91, 121.63, 111.43, 65.90, 61.41, 16.39, and 14.34. (2,6-Difluoro-phenoxy)-acetic acid ethyl ester (1.66 g) was dissolved in ethanol (10.0 mL), NaOH (2 eqv's) and 5 drops of H$_2$O was added and the reaction stirred at room temperature overnight. The product was filtered and dried to give a white solid, 1.11 g, 64% yield. $^1$H NMR (400 MHz, d-DMSO): σ 4.84 (s, 2H), 7.31 (m, 1H), 7.46 (m, 1H), 7.93 (m, 1H), 13.19 (s, 1H)

EP-000188

((1S,2R)-1-benzyl-2-hydroxybut-3-enyl)carbamic acid tert-butyl ester (0.145 g, 0.523 mmol, 1.0 equiv), N-tert-butyl-2-iodobenzamide (0.190 g, 0.628 mmol, 1.2 equiv), bis(benzonitrile)dichloro palladium(II) (0.020 g, 0.0523 mmol, 0.1 equiv), sodium acetate (0.171 g, 2.09 mmol, 4.0 equiv), and N,N-dimethylglycine (0.108 g, 1.05 mmol, 2.0 equiv) were combined in N-methylpyrrolidinone (4 mL, 0.13M) and degassed three times by reducing the pressure for several minutes and then purging with nitrogen. This solution was heated to 120° C. for 14 hrs. It was then quenched with sat. NaHCO$_3$ solution (10 mL), extracted with ethyl acetate (2×10 mL), the combined organic pool was washed with brine (1×10 mL), dried (MgSO$_4$) filtered and concentrated in vacuo. It was chromatographed using the Biotage 12M column with 40% ethyl acetate in hexanes. An off-white amorphous solid was obtained (0.151 g, 64%). ESMS: 475(M+23), 453(M+1)

EP-000776

To EP-000188 (0.074 g, 0.164 mmol) in ethanol (10 mL, 0.2M) was added the platinum (IV) oxide (7 mg, 10 wt %) and allowed to stir under a atmosphere of hydrogen (1 atm) overnight. The catalyst was filtered through a pad of celite, concentrated in vacuo, and chromatographed using the Biotage 12M column with 40% ethyl acetate in hexanes. A colorless solid was obtained (0.042 g, 56%). ESMS: 477 (M+23), 455(M+1).

EP-000245

The desired compound was prepared in the following manner: EP-000776 (0.1 mmol) was dissolved in a solution of 8M HCl in dioxane (1 mL), and this was stirred for 20 min. This solution was concentrated in vacuo, and the residue dissolved in CH$_2$C$_2$(0.1M). The NMM (0.2 mmol, 2.0 equiv) and benzoyl chloride (0.2 mmol, 2.0 equiv) were added. After stirring at RT overnight, the reaction was quenched with sat. NaHCO$_3$ solution, extracted with ethyl acetate, the combined organic pool was washed with brine, dried (MgSO$_4$), filtered and concentrated in vacuo. It was chromatographed using a Biotage column and 20% ethyl acetate in hexanes. The title compound was obtained as an amorphous solid (0.06 mmol, 60%). $^1$H NMR (400 MHz, CDCl$_3$) δ7.8 (d, 3.4H), 7.3–7.1 (m, 14H), 6.5 (d, 1.6H), 5.8 (d, 3.1H), 4.1 (m, 1.8H), 3.9 (m, 1.3H), 3.5 (d, 2H), 3.4 (d, 1.2H), 2.9–2.7 (m, 5.2M), 1.4 (br s, 9H).

EP-000244

The desired compound was prepared in the following manner: EP-000776 (0.1 mmol) was added a solution of 8M HCl in dioxane (1 mL) and this was stirred for 20 min. The dioxane was then removed in vacuo, and the residue was dissolved in CH$_2$Cl$_2$ (0.1M). The N-methylmorpholine (0.3 mmol, 3.0 equiv) was added followed by the EDCI (0.2 mmol, 2.0 equiv), HOBT (0.2 equiv, 2.0 equiv) and the phenoxyacetic acid (0.1 mmol, 1.0 equiv). After stirring at RT overnight, the reaction was quenched with sat. NaHCO$_3$ solution, extracted with ethyl acetate, the combined organic pool was washed with brine, dried (MgSO$_4$), filtered and concentrated in vacuo. It was chromatographed using a Biotage column and 20% ethyl acetate in hexanes. The title compound was obtained as an amorphous solid (0.05 mmol, 50%) ESMS: 489(M+23).

EP-000895

Using essentially the same procedure as for the preparation of EP-000244, EP-000776 (0.1 mmol) was first reacted with 8M HCl in dioxane solution (1 mL) followed by the NMM (0.3 mmol, 3.0 equiv), EDCI (0.2 mmol, 2.0 equiv), HOBT (0.2 equiv, 2.0 equiv) and the 5-hydroxymethyl-2-methylbenzoic acid (0.1 mmol, 1.0 equiv) in CH$_2$Cl$_2$ to give the title compound as an amorphous solid (0.06 mmol, 60%) ESMS: 525(M+23), 503(M+1).

EP-000242

Using essentially the same procedure as for the preparation of EP-000244, EP-000188 (0.1 mmol) was first-reacted with 8M HCl in dioxane solution (1 mL) followed by the NMM (0.3 mmol, 3.0 equiv), EDCI (0.2 mmol, 2.0 equiv), HOBT (0.2 equiv, 2.0 equiv) and the (S)-2-hydroxypropionic acid sodium salt (0.1 mmol, 1.0 equiv) in CH$_2$Cl$_2$ to give the alkene corresponding to the title compound. The alkene was then reduced following essentially the same procedure as for EP-000776 using 10 mol % platinum (IV) oxide in ethanol. The title compound was obtained as an amorphous solid (0.06 mmol, 60%). ESMS: 449(M+23), 427(M+1).

EP-000241

Using essentially the same procedure as for the preparation of EP-000244, EP-000188 (0.1 mmol) was first reacted with 8M HCl in dioxane solution (1 mL) followed by the NMM (0.2 mmol, 2.0 equiv) and phenothiazine-10-carbonyl chloride (0.1 mmol, 1.0 equiv) in CH$_2$Cl$_2$ to give the alkene corresponding to the title compound. The alkene was then reduced following essentially the same procedure as for EP-000776 using 10 mol % platinum (IV) oxide in ethanol. The title compound was obtained as an amorphous solid (0.05 mmol, 50%). ESMS: 580(M+1), 602(M+23)

EP-000243

Using essentially the same procedure as for the preparation of EP-000244, EP-000188 (130 mg) was first reacted with 8M HCl in dioxane solution (10 mL) followed by NMM (9 μL), EDCI (115 mg), HOBT (92 mg) and 2-phenoxypropionic acid (49.4 mg) in CH$_2$Cl$_2$ to give the alkene corresponding to the title compound. The alkene was then reduced following essentially the same procedure as for EP-000776 using 10 mol % platinum (IV) oxide in ethanol. The title compound was obtained as an amorphous solid (0.05 mmol, 50%). ESMS: 503.38(M+1), 525.36(M+23)

EP-000180

Using essentially the same procedure as for the preparation of EP-000244, ((1S,2R)-1-benzyl-2-hydroxybut-3-enyl)carbamic acid tert-butyl ester (0.330 g) was first reacted with 8M HCl in dioxane solution (1 mL) followed by NMM (0.62 mL), and (S)-tetrahydro-furan-3-chloroformate (0.227 g) in CH$_2$Cl$_2$ The carbamate from above was subjected to essentially the same procedure as for EP-000188 using N-tert-butyl-2-iodobenzamide (0.227 g), bis(benzonitrile) dichloro palladium(II) (0.019 g), sodium acetate (0.164 g), and N,N-dimethylglycine (0.103 g) in N-methylpyrrolidinone (4 mL, 0.13M). The resulting alkene was then reduced following essentially the same procedure as for EP-000776 using 10 mol % platinum (IV) oxide in ethanol. The title compound was obtained as an amorphous solid (57 mg 11%) ESMS: 469.45(M+1)

EP-000373

Using essentially the same procedure as for the preparation of EP-000245, EP-000776 (0.1 mmol) was first reacted with 8M HCl in dioxane solution (1 mL) followed by the NMM (0.2 mmol, 2.0 equiv) and ethyl chloroformate (0.1 mmol, 1.0 equiv) in CH$_2$Cl$_2$ to give the title compound as an amorphous solid (0.06 mmol, 60%). ESMS: 427.80(M+1), 449.77 (M+23).

EP-000762

Using essentially the same procedure as for the preparation of EP-000245, EP-000776 (0.1 mmol) was first reacted with 8M HCl in dioxane solution (1 mL) followed by the NMM (0.2 mmol, 2.0 equiv) and phenyl acetyl chloride (0.1 mmol, 1.0 equiv) in CH$_2$Cl$_2$ to give the title compound as an amorphous solid (0.06 mmol, 60%) ESMS 473(M+1), 495 (M+23).

EP-000763

Using essentially the same procedure as for the preparation of EP-000245, EP-000776 (0.1 mmol) was first reacted with 8M HCl in dioxane solution (1 mL) followed by the NMM (0.2 mmol, 2.0 equiv) and 3-phenylpropionyl chloride (0.1 mmol, 1.0 equiv) in CH$_2$Cl$_2$ to give the title compound as an amorphous solid (0.06 mmol, 60%). ESMS 509(M+23), 487(M+1).

EP-000760

Using essentially the same procedure as for the preparation of EP-000244, EP-000776 (0.1 mmol) was first reacted with 8M HCl in dioxane solution (1 mL) followed by the NMM (0.3 mmol, 3.0 equiv), EDCI (0.2 mmol, 2.0 equiv), HOBT (0.2 equiv, 2.0 equiv) and the (2-naphthoxy)acetic acid (0.1 mmol, 1.0 equiv) in CH$_2$Cl$_2$ to give the title compound as an amorphous solid (0.05 mmol, 50%). ESMS: 561(M+23), 539(M+1).

EP-000771

Using essentially the same procedure as for the preparation of EP-000245, EP-000776 (0.1 mmol) was first reacted with 8M HCl in dioxane solution (1 mL) followed by the NMM (0.2 mmol, 2.0 equiv) and ethyl isocyanate (0.1 mmol, 1.0 equiv) in CH$_2$Cl$_2$ to give the title compound as an amorphous solid (0.05 mmol, 50%). ESMS: 449(M+23), 426(M+1)

EP-000179

Using essentially the same procedure for the preparation of EP-000188, ((1S,2R)-1-benzyl-2-hydroxybut-3-enyl) carbamic acid tert-butyl ester ester (2.77 g, 10.0 mmol, 1.0 equiv), 2-bromobenzoic acid methyl ester (1.66 mL, 12.0 mmol, 1.2 equiv), bis(benzonitrile)dichloro palladium(II) (0.0.38 g, 1.0 minol, 0.1 equiv), sodium acetate (2.46 g, 30 mmol, 3.0 equiv), and N,N-dimethylglycine (2.06 g, 20.0 mmol, 2.0 equiv) were combined in N-methylpyrrolidinone (50 mL). The resulting material was chromatographed using the Biotage 40 L column with 40% ethyl acetate in hexanes. A colorless, amorphous solid was obtained in 22% yield. ESMS: 434(M+23), 294(M+1).

2-((3R,4S)-4-tert-butoxycarbonylamino-3-hydroxy-5-phenylpentyl)benzoic Acid Methyl Ester Using essentially the same procedure for the preparation of EP000766, 2-((E) (3R,4S)-4tert-butoxycarbonylamino-3-hydroxy-5-phenylpent-1-enyl)benzoic acid methyl ester 7 (0.057 g, 0.139 mmol) in ethanol (14 mL) was mixed with platinum (IV) oxide (6mg, 10 wt %) and allowed to stir under atmosphere of hydrogen overnight. The resulting material was chromatographed using the Biotage 12S column with 20% ethyl acetate in hexanes. A colorless solid was obtained (0.021 g, 37%) ESMS: 436(M23).EP-001054 To 2-((3R,4S)-4-tert-butoxycarbonylamino-3-hydroxy-5-phenylpentyl)benzoic acid methyl ester (0.1 mmol) in MeOH (10 mL) was added aq. 6M NaOH (100 equiv), and this solution was stirred at RT for 4 hrs. The reaction was quenched with an aq. 10% HCl solution, extracted with ethyl acetate, the organic pool was washed with brine, dried (MgSO$_4$), filtered and concentrated in vacuo. This residue was redissolved in CH$_2$Cl$_2$ (1 mL), and to this was added the NMM (0.26 mmol, 2.6 equiv), EDCI (0.2 mmol, 2.0 equiv), HOBT (0.2 mmol, 2.0 equiv) and the (S)-F4 (+)-2-phenylglycinol (0.1 mmol, 1.0 equiv). This solution was stirred at RT overnight. It was quenched with sat. NaHCO$_3$ solution, extracted with ethyl acetate, the combined organic pool was washed with brine, dried (Na$_2$SO$_4$) filtered and conc. in vacuo. The title compound was obtained as an amorphous solid (0.05 mmol, 50%). ESMS: 541(M+23).

EP-001053.

Using essentially the same procedure for the preparation of EP-001054, the 2-((3R,4S)-4-tert-butoxycarbonylamino-3-hydroxy-5-phenylpentyl)benzoic acid methyl ester (0.1 mmol) was first reacted with the aq. 6M NaOH (100 equiv) in MeOH, followed by the NMM (0.26 mmol, 2.6 equiv), EDCI (0.2 mmol, 2.0 equiv), HOBT (0.2 mmol, 2.0 equiv) and the (R)-(-)-2-phenylglycinol (0.1 mmol, 1.0 equiv) in CH$_2$Cl$_2$ to give the title compound as an amorphous solid (0.05 mmol, 50%) ESMS: 540(M+23).

EP-000766

Using essentially the same procedure for the preparation of EP-001054, the 2-((3R,4S)-4-tert-butoxycarbonylamino-3-hydroxy-5-phenylpentyl)benzoic acid methyl ester (0.1 mmol) was first reacted with the aq. 6M NaOH (100 equiv) in MeOH, followed by the NMM (0.26 mmol, 2.6 equiv), EIDCI (0.2 mmol, 2.0 equiv), HOBT (0.2 mmol, 2.0 equiv) and the isoamylamine (0.1 mmol, 1.0 equiv) in CH$_2$Cl$_2$ to give the title compound as an amorphous solid (0.05 mmol, 50%) ESMS: 491(M+23), 469(M+1).

EP-000156

Using essentially the same procedure for the preparation of EP-001054, the 2-((3R,4S)-4-tert-butoxycarbonylamino-3-hydroxy-5-phenylpentyl)benzoic acid methyl ester (0.1 mmol) was first reacted with the aq. 6M NaOH (100 equiv) in MeOH, followed by the NMM (0.26 mmol, 2.6 equiv), EDCI (0.2 mmol, 2.0 equiv), HOBT (0.2 mmol, 2.0 equiv) and the isobutylamine (0.1 mmol, 1.0 equiv) in CH$_2$Cl$_2$ to give the title compound as an amorphous solid (0.05 mmol, 50%) ESMS: 477(M+23), 455(M+1).

EP-000770

Using essentially the same procedure for the preparation of EP-000245, EP-000766 (0.0 mmol) was first reacted with 8M HCl in dioxane solution (0.1M) followed by the NMM (0.1 mmol, 2.0 equiv) and ethyl chloroformate (0.05 mmol, 1.0 equiv) in $CH_2Cl_2$ to give the title compound as an amorphous solid (0.025 mmol, 50%). ESMS: 463(M+23), 441(M+1).

EP-000981

Using essentially the same procedure for the preparation of EP-000188, the ((1S,2R)-1-benzyl-2-hydroxybut-3-enyl) carbamic acid tert-butyl ester (0.554 g, 2 mmol, 1.0 equiv), N-tert-butyl-5-hydroxy-2-iodobenzamide (0.638 g, 2 mmol, 1.0 equiv), bis-(benzonitrile)dichloro palladium(II) (0.0767 g, 0.2 mmol, 0.1 equiv), sodium acetate (0.328 g, 4 mmol, 2.0 equiv), and N,N-dimethylglycine (0.412 g, 4 mmol, 2.0 equiv) were combined in N-methylpyrrolidinone. The resulting material was subjected to essentially the same procedure as for the preparation of EP-000776.

The resulting compound (0.094 g, 0.2 mmol) was dissolved in 5 mL of acetone to which was added $K_2CO_3$ (0.041 g, 0.3 mmol) and benzyl bromide (24 μl, 0.2 mmol). The mixture was refluxedovernight and filtered. The filtrate was concentrated and purified by flash chromatography using 4:1 hexanes:ethyl acetate to give the 0.085 g of the title compound as an amorphous solid. $^1$H NMR (400 MHz, $CDCl_3$) δ7.5–7.3 (m, 8H), 7.2–7.0 (m, 3H), 5.9 (br s, 1H), 5.1 (s, 3H), 4.9 (m, 1H), 4.2 (m, 1H), 3.0 (m, 2H), 2.8 (m, 2H), 1.8 (m, 1H), 1.6 (m, 4H), 1.4 (brs, 25H).

EP-000849

Using essentially the same procedure for the preparation of EP-000188, the ((1S,2R)-1-benzyl-2-hydroxybut-3-enyl) carbamic acid tert-butyl ester 1 (0.337 g, 1.1 mmol, 1.1 equiv), 1-bromonaphthalene-2-carboxylic acid tert-butlamide (0.277 g, 1 mmol, 1.0 equiv), bis-(benzonitrile) dichloro palladium(II) (0.038 g, 0.1 mmol, 0.1 equiv), sodium acetate (0.328 g, 4 mmol, 4.0 equiv), and N,N-dimethylglycine (0.206 g, 2 mmol, 2.0 equiv) were combined in N-methylpyrrolidinone (8 mL). The resulting material was subjected to essentially the same procedure as for the preparation of EP-000776 and chromatographed on silica gel to give the title compound as an amorphous solid (0.5 mmol, 50%). ESMS: 527(M+23), 505(M+1).

EP-000857

Using essentially the same procedure as for the preparation of EP-000245, EP-000849 (0.5 mmol) was first reacted with 8M HCl in dioxane solution (1 mL) followed by the NMM (0.1 mmol, 2.0 equiv) and ethyl chloroformate (0.05 mmol, 1.0 equiv) in $CH_2Cl_2$ to give the title compound as an amorphous solid (0.025 mmol, 50%). ESMS: 499(M+23), 477(M+1).

EP-001496

EP-000776 (2.21 g, 4.45 mmol) was dissolved in 30% ($TFA:CH_2Cl_2$) and stirred at room temperature for 1 hour. The reaction was made basic with sodium bicarbonate, extracted with $CH_2Cl_2$, dried with $Na_2SO_4$ and the solvent was removed in vacuo to give a pale yellow solid. ESM: 355 (M+1)

EP-001214

(2,6-Difluoro-phenoxy)-acetic acid (0.062 mg, 0.330 mmol) and EP-001496 (0.150 g, 0.330 mmol) were dissolved in 2.0 mL of dry DMF. HOBT (0.045 g, 0.330 mmol) was added followed by HBTU (0.125 g, 0.330 mmol) and, NMM (0.100 g, 0.109 mL, 0.990 mmol and the reaction stirred at room temperature overnight. The DMP was removed in vacuo, the residue was dissolved in dichloromethane and washed with 10 mL of 1 N HCL, 10 mL of sat'd $NaHCO_3$, 10 mL of water and 10 mL of brine, dried with $Na_2SO_4$. The solvent was removed in vacuo to give an oily residue that was subjected to column chromatography (silica gel, 70:30 ethyl acetate:hexanes) that provided 0.074 g, 43% yield as a white solid. $^1$H NMR (400 MHz, $CDCl_3$): 7.2 (m, 9H), 6.95 (m, 2H), 6.85 (m, 2H), 5.81 (s, 1H), 5.25 (s, 1H), 4.31 (dd, J=1.11 Hz, 67.8 Hz, 2H), 4.16 (m, 1H), 3.45 (m, 1H), 3.03 (dd, J=3.3 Hz, 7.2 Hz, 1H), 2.93 (m, 1H), 2.76 (m, 2H), 1.90 (m, 2H), 1.42 (s, 9H).

EP-001215

Using substantially the same procedure as for EP-001214, (2-Chloro-6methyl-phenoxy)acetic acid (0.066 g, 0.33 mmol) and EP-001496 (0.150 g, 0.330 mmol) were dissolved in 2.0 mL of dry $CH_2C_2$. HOBT (0.045 g, 0.330 mmol) was added followed by EDCI (0.65 g, 0.330 mmol) and NMM (0.100 g, 0.109 mL, 0.990 mmol). The desired product was obtained after column chromatography (silica gel, 70:30 ethyl acetate: hexanes), as a as a white solid (0.072 g, 41% yield). $^1$H NMR (400 MHz, $CDCl_3$): 7.30 (t, J=7.6 Hz, 1H), 7.20 (m, 8H), 7.03 (s, 1H), 7.00 (d=8.0 Hz, 1H), 6.90 (t, J=7.6 Hz, 1H), 5.85 (s, 1H), 4.24 (m, 1H), 4.13 (dd, J=14.4 Hz, 2H), 3.47 (m, 1H), 3.09 (dd, J=4.7 Hz, 48.8 Hz, 1H), 2.93 (m, 1H), 2.78 (m, 2H), 2.12 (s, 3H), 1.92 (m, 2H), 1.43 (s, 9H).

EP-001217

Using substantially the same procedure as for EP001214, (2-Fluoro-6methoxy-phenoxy)-acetic acid (0.097 g, 0.423 mmol) and EP-001496 (0.150 g, 0.423 mmol) were dissolved in 2.0 mL of dry $CH_2Cl_2$. HOBT (0.057 g, 0.423 mmol) was added followed by EDCI (0.081 g, 0.423 mmol) and NMM (0.128 g, 0.140 mL, 1.27 mmol). The desired product was obtained after column chromatography (silica gel, 70:30 ethyl acetate: hexanes), as a as a white solid (0.107 g, 47% yield). $^1$H NMR (400 MHz, $CDCl_3$): 7.54 (d, J=9.6 Hz, 1H), 7.20 (m, 8H), 6.94 (q, J=7.2 Hz, 1H), 6.67 (t, J=9.2 Hz, 1H), 6.60 (d, J=8.4 Hz, 1H), 5.81 (s, 1H), 5.23 (s, 1H), 4.30 (q, J=15.6 Hz, 2H), 4.15 (m, 1H), 3.68 (s, 3H), 3.42 (m, 1H), 3.01 (dd, J=4.4 Hz, J=9.6 Hz, 2H), 2.93 (m, 1H), 2.75 (m, 2H), 1.87 (m, 1H), 1.42 (s, 9H).

EP-001218

Using substantially the same procedure as for EP-001214, (2,6-Dimethyl-4-bromo-phenoxy)-acetic acid (0.121 g, 0.423 mmol) and EP-001496 (0.150 g, 0.423 mmol) were dissolved in 2.0 mL of dry $CH_2Cl_2$. EDCI (0.081 g, 0.423 mmol) and NMM (0.128 g, 0.140 mL, 1.27 mmol) were added the desired product was obtained after column chromatography (silica gel, 70:30 ethyl acetate:hexanes), as a as a white solid (0.98 g, 39% yield). $^1$H NMR (400 MHz, $CDCl_3$): 7.32 (t, J=9.6 Hz, 1H), 7.21 (m, 9H), 6.96 (d, J=15.4 Hz, 1H), 5.77 (s, 1H), 5.35 (s, 1H), 4.25 (m, 1H), 3.93 (dd, J=19.7 Hz, 63.4 Hz), 3.48 (m, 1H), 3.07 (dd, J=4.8 Hz, 13.8 Hz, 1H), 2.93 (m, 1H), 2.78 (m, 2H), 2.02 (s, 6H), 1.92 (m, 2H), 1.43 (s, 9H).P-001213. Using substantially the same procedure as for EP-001214, (2-Methoxy-6-methylphenoxy)acetic acid (0.095 g, 0.423 mmol) and EP-001496 (0.150 g, 0.423 mmol) were dissolved in 2.0 mL of dry $CH_2Cl_2$. EDCI (0.081 g, 0.423 mmol) and NMM (0.128 g, 0.140 mL, 1.27 mmol) were added. The desired product was obtained after column chromatography (silica gel, 70:30 ethyl acetate:hexanes), as a as a white solid (0.081 g, 36% yield). $^1$H NMR (400 MHz, $CDCl_3$): 7.45 (d, J=9.2 Hz, 1H), 7.19 (m, 8H), 6.91 (t, J=6.6 Hz, 1H), 6.69 (m, 2 H), 5.83 (s, 1H), 5.27, (s, 1H), 4.19 (m, 1H), 4.18 (dd, J=15.2 Hz, 31.6 Hz, 2H), 3.75 (s, 3H), 2.87 (m, 5H), 2.13 (s, 3H), 1.43 (s, 9H).

EP-001224

Using substantially the same procedure as for EP-001214, (2,4,6-Trichloro-phenoxy)-acetic acid (0.108 g, 0.423 mmol) and EP-001496 (0.150 g, 0.423 mmol) were dissolved in 2.0 mL of dry $CH_2Cl_2$. EDCI (0.081 g, 0.423 mmol) and NMM (0.128 g, 0.140 mL, 1.27 mmol) were added the desired product was obtained after column chromatography (silica gel, 70:30 ethyl acetate:hexanes), as a as a white solid (0.061 g, 24% yield. $^1$H NMR (400 MHz, $CDCl_3$): 7.22 (m, 11H), 5.77 (s, 1H), 5.34 (s, 1H), 4.24 (m, 1H), 4.22 (dd, J=14.0 Hz, J=45.2 Hz, 2H), 3.46 (m, 1H), 3.07 (dd, J=4.4 Hz, J=10.0 Hz, 1H), 2.94 (s, 1H), 2.79 (m, 2H), 1.91 (m, 2H), 1.43 (s, 9H).

EP-001225

Using substantially the same procedure as for EP-001214, (2,6-Dibromo4-methyl-phenoxy)acetic acid (0.137 g, 0.423 mmol) and EP-001496 (0.150 g, 0.423 mmol) were dissolved in 2.0 mL of dry $CH_2Cl_2$. EDCI (0.081 g, 0.423 mmol) and NMM (0.128 g, 0.140 mL, 1.27 mmol) were added. The desired product was obtained after column chromatography (silica gel, 70:30 ethyl acetate:hexanes), as a as a white solid (0.108 g, 38% yield). $^1$NMR (400 MHz, $CDCl_3$): 7.22 (m, 11H), 7.01 (d, J=9.2 Hz, 1H), 5.81 (s, 1H), 5.26 (d, J=4.4 Hz, 1H), 4.23 (m, 1H), 4.22 (dd, J=14.4 Hz, J=16.4 Hz, 2H), 3.47 (m, 1H), 3.09 (dd, J=4.4 Hz, 9.6 Hz, 1H), 2.92 (m, 1H), 2.78 (m, 2H), 2.22 (s, 3H), 1.91 (m, 2H), 1.43 (s, 9H). $^{13}$C NMR ($CDCl_3$): 169.37, 156.36, 131.13, 127.51, 126.91, 121.63, 111.43, 65.90, 61.41, 16.39, and 14.34.

EP-001227

Using substantially the same procedure as for EP-001214, (2,3,4-Trifluoro-phenoxy)-acetic acid (0.087 g, 0.423 mmol) and EP-001496 (0.150 g, 0.423 mmol) were dissolved in 2.0 mL of dry $CH_2Cl_2$. EDCI (0.081 g, 0.423 mmol) and NMM (0.128 g, 0.140 mL, 1.27 mmol) were added. The desired product was obtained after column chromatography (silica gel, 70:30 ethyl acetate:hexanes), as a as a white solid (0.036 g, 16% yield). $^1$H NMR (400 MHz, $CDCl_3$): σ7.32 (t, J=7.6 Hz, 1 H), 7.21 (m, 9 H), 6.70 (t, J=7.6 Hz, 1 H), 6.35 (m, 1H), 5.75 (s, 1H), 5.41 (d, J=3.6 Hz, 1H), 4.22 (dd, J=14.8 Hz, J=16.5 Hz, 2H), 4.20 (m, 1H), 3.39 (m, 1H), 3.01 (dd, J=4.4 Hz, 9.6 Hz, 1H), 2.91 (m, 1H), 2.75 (m, 2H), 1.86 (m, 2H), 1.43 (s, 9H).

EP-001242

EP-000776 (1.0 g, 2.20 mmol) was dissolved in 15.0 mL of $CH_2Cl_2$, acetic anhydride (2.25 g, 2.10 mL, 22.0 mmol) was added followed by pyridine (0.35 g, 0.36 mL, 4.40 mmol) and the reaction was allowed to stir at room temperature overnight. The reaction was poured into a separatory funnel, washed with 1 N HCl (3×35 mL), $H_2O$ (1×35 mL), sat'd $NaHCO_3$ (35 mL) and brine (35 mL), dried with $Na_2SO_4$ and the solvent removed in vacuo to give 0.80 g as a pale yellow solid, 75% yield. The boc group was removed using the same procedure as for EP-001496 and the free amine (0.291 g, 0.734 mmol was reacted with (S)-(-)-2-hydroxyisocaproic acid (0.098 g, 0.734 mmol), EDCI (0.141 g, 0.734 mmol), HOBT (0.099 g, 0.734 mmol), and NMM (0.222 g, 0.242 mL, 2.20 mmol) in 2.0 mL of dry $CH_2Cl_2$, at room temperature overnight. The residue was washed with 10 mL of 1 N HCL,10 mL of sat'd $NaHCO_3$, 10 mL of water and 10 mL of brine, dried with $Na_2SO_4$. The solvent was removed in vacuo to give the alcohol as an oily residue that was subjected to column chromatography (silica gel, 70:30 ethyl acetate:hexanes) that provided 0.183 g, 49% yield as a white solid. The alcohol from above (0.05 g, 0.098 mmol) was dissolved in dry $CH_2C_2$ and cooled in an ice bath, methanesulfonyl chloride (0.011 g, 0.098 mmol) was added drop wise, $Et_3N$ (0.015 g, 0.008 mL, 0.147 mmol) was added and the reaction was allowed to stir at room temperature for 4 hours. The solvent was removed in vacuo and the residue was dissolved in 0.5 mL of dry THF. In another flask 0.006 g, (0.058 mmol) of 2-methyl phenol was dissolved in 0.5 mL dry THF and cooled in an ice bath, NaH (0.003 g, 0.064 mmol) was added and the mixture was stirred at room temperature for 30 minutes at which time the mesylate generated above was added and the reaction was allowed to stir at room temperature overnight. The reaction was poured onto water and extracted with ethyl acetate (3×10 mL), the organic layers were combined and washed with water (1×10 mL), brine (1×10 mL) and dried with $N_2SO_4$, and the solvent was removed in vacuo to give the acetate protected material 0.022 g, 71% yield as a pale yellow solid, which was carried crude into the next reaction. $^1$H NMR (400 MHz, $CDCl_3$): 7.15 (m, 12H), 6.81 (m, 1H), 6.10 (s, 1H), 5.67 (s, 1H), 5.08 (s, 1H), 4.33 (m, 1H), 4.10 (m, 1H), 3.10 (dd, J=4.4 Hz, J=9.8 Hz, 1H), 3.03 (m, 1H), 2.78 (m, 1H), 2.57 (m, 1H), 2.17 (s, 3H), 1.61 (m, 3H), 0.75 (dd, J=6.8 Hz, J=25.2 Hz, 6H). The acetate protected material (0.023 g, 0.038 mmol) was dissolved in 1.0 mL of methanol, $K_2CO_3$ (0.013 g, 0.096 mmol) was added and the reaction was allowed to stir at room temperature for 1 hour. The reaction was filtered through a plug of cotton and the solvent removed in vacuo to give 0.018 g as a white solid, which was subjected to column chromatography (silica gel, 70:30 hexanes:ethyl acetate) that provided 0.007 g, 33% as a white solid.

EP-000901, EP-000955, EP-000966, EP-000969, EP-000970

The appropriate acid chlorides (0.062 mmol) were placed in a vial; anhydrous $CH_2Cl_2$ (0.50 mL), EP-0001496 (0.63 mmol), and DIEA (0.016 g, 0.022 mL, 0.124 mmol) were added and the reaction was placed on a shaker overnight. The solvent was removed in vacuo and the residue. was taken up in 50:50 (ethyleacetate:hexanes) and put through a plug of silica and $MgSO_4$, the solvent was removed in vacuo and the compounds were subjected to LC/MS. ESMS: EP-000901, 495 (M+1); EP-000955, 528 (M+1); EP-000966, 519 (M+1495 (M+1); EP-000970, 528 (M+1)

EP-000943, EP-000949, EP-000951, EP-000972, EP-000973

The appropriate acids (0.056 mmol) were placed in vials. Anhydrous $CH_2Cl_2$ (0.50 mL), oxalyl chloride (0.008 g, 0.006 mL, 0.062 mmol), and a drop of anhydrous DMF were added to each vial and the reactions were allowed shake at room temperature for 4 hours. The vials were place under high vac until dry, to the residue was added anhydrous $CH_2Cl_2$ (0.50 mL), EP-001496 (0.020 g, 0.056 mmol) and DIEA (0.014 g, 0.020 mL, 0.112 mmol) and the reactions were left to shake at room temperature overnight. The solvent was removed in vacuo and the residue was taken up in 50:50 (ethyl acetate:hexanes) and put through a plug of silica and $MgSO_4$, the solvent was removed in vacuo and the compounds were subjected to LC/MS. ESMS: EP-000943, 475 (M+1); EP-000949, 488 (M+1); EP-000951, 487 (M+1); EP-000972, 489 (M+1); EP-000973, 533 (M+1)

EP-000874, EP-000878, EP-000880

The appropriate sulfonyl chlorides (0.047 mmol) were placed in vials. Anhydrous $CH_2Cl_2$ (0.05 mL), EP-001496 (0.012 g, 0.047 mmol), and pyridine (0.014 g, 0.014 mL, 0.018 mmol) were added and the reactions were allowed to shake at room temperature overnight. The solvent was removed in vacuo and the residue was taken up in 50:50 (ethyl acetate:hexanes) and put through a plug of silica and $MgSO_4$, the solvent was removed in vacuo and the compounds were subjected to LC/MS. ESMS: EP-000874, 523 (M+1); EP-000878, 546 (M+1); EP-000880, 501 (M+1)

EP-000344

To 2-((3R,4S)-4-tert-butoxycarbonylamnino-3-hydroxy-5-phenylpentyl)benzoic acid (0.029 g, 0.073 mmol) and butyl amine (0.005 g, 0.073 mmol) were dissolved in 1.0 mL of dry CH$_2$Cl$_2$. HOBT (0.009 g, 0.073 mmol) was added followed by EDCI (0.011 g, 0.3073 mmol). NMM (0.015 g, 0.016 mL, 0.145 mmol) was added and the reaction stirred at room temperature overnight. The organic layer was washed with water and brine, dried with Na$_2$SO$_4$. The solvent was removed in vacuo to provide 4.7 mg, 16% yield as a white solid. ESMS: 455 (M+1)

EP-001008

Morpholine-N-acetyl chloride (0.042 g, 0.282 mmol) and EP-001496 (0.10 g, 0.282 mmol) were dissolved in anhydrous CH$_2$Cl$_2$, NMM (0.086 g, 0.093 mL, 0.846 mmol) was added and the reaction stirred at room temperature overnight. The urea product crashed out of solution, was filtered and dried to give 0.079 g, 61% yield as a white solid. ESMS: 490 (m+1)

EP-000891

The appropriate butyl isocyanate (0.042 mmol), EP-001496 (0.015 g, 0.042 mmol), and CH$_2$Cl$_2$ (1 mL) were placed in vials and allowed to stir at room temperature overnight. Solvent was removed to give the ureas. ESMS: 454 (m+1)

EP-001246

Using substantially the same procedure as for EP-001214, (0.197 g, 0.665 mmol) of (3-hydroxy-2-methyl-phenoxy)-acetic acid and EP-001496 (0.236 g, 0.665 mmol) were dissolved in 3.5 mL of dry CH$_2$Cl$_2$. EDCI (0.140 g, 0.732 mmol) was added followed by NMM (0.220 g 0.214 mL, 2.19 mmol) and the reaction stirred at room temperature overnight. The residue was washed with 1 N HCL, sat'd NaHCO$_3$, water and brine, dried with Na$_2$SO$_4$. The solvent was removed in vacuo to give an oily residue that was subjected to column chromatography (silica gel, 70:30 ethyl acetate:hexanes) that provided 0.038 g, 12% yield as a white solid. $^1$H NMR (300 MHz, CDCl$_3$): 7.22 (m, 10H), 6.83 (m, 2H), 6.48 (d, 1H), 6.08 (d, 1H), 5.82 (s, 1H), 4.23 (m, 2H), 4.08 (m, 1H), 3.51 (m, 1H), 2.96 (m, 2H), 2.77 (m, 2H), 1.96 (s, 3H), 1.90 (m, 2H), 1.43 (s, 9H)

EP-001173

Using substantially the same procedure as for EP-001214, (0.047 g, 0.282 mmol) of (2-methyl-phenoxy)-acetic acid and EP-001496 (0.100 g, 0.282 mmol) were dissolved in 2.0 mL of dry CH$_2$Cl$_2$. HOBT (0.042 g, 0.310 mmol) was added followed by EDCI (0.059 g, 0.310 mmol). NMM (0.094 g 0.102 mL, 0.931 mmol) was added and the reaction stirred at room temperature overnight. The residue was washed with 1 N HCL, sat'd NaHCO$_3$, water and brine, dried with Na$_2$SO$_4$. The solvent was removed in vacuo to give an oily residue that was subjected to column chromatography (silica gel, 70:30 ethyl acetate:hexanes) that provided 0.0723 g, 51% yield as a white solid. $^1$H NMR (300 MHz, CDCl$_3$): 7.17 (m, 11H), 6.93 (m, 2H), 6.30 (m, 1H), 5.77 (s, 1H), 5.52 (s, 1H), 4.20 (dd, 2H), 4.23 (m, 2H), 3.41(m, 1H), 3.03 (dd, 1H), 2.93 (m, 1H), 2.76 (m, 2H), 2.19 (2, 3H), 1.88 (m, 2H), 1.45 (s, 9H) ESMS: 569.81 (M+1), 591.78 (M+23)

EP-001185

Using substantially the same procedure as for EP-001214, (0.094 g, 0.561 mmol) of (3-methyl-phenoxy)-acetic acid and EP-001496 (0.200 g, 0.564 mmol) were dissolved in 3.0 mL of dry CH$_2$Cl$_2$. HOBT (0.084 g, 0.620 mmol) was added followed by EDCI (0.119 g, 0.620 mmol). NMM (0.188 g 0.205 mL, 1.86 mmol) was added and the reaction stirred at room temperature overnight. The residue was washed with 1 N HCL, sat'd NaHCO$_3$, water and brine, dried with Na$_2$SO$_4$. The solvent was removed in vacuo to give an oily residue which was subjected to column chromatography (silica gel, 70:30 ethyl acetate:hexanes) which provided 0.033 g, 12% yield as a white solid $^1$H NMR (300 MHz, CDCl$_3$): 7.18 (m, 9H), 6.78 (m, 2H), 6.62 (s, 1H), 6.57 (m, 1H), 5.88 (s, 1H), 5.42 (d, 2H), 4.20 (dd, 2H), 4.18 (m, 2H), 3.42 (m, 1H), 2.96 (m, 2H), 2.76 (m, 2H), 1.87 (m, 2H), 1.45 (s, 9H) ESMS: 503.68 (M+1), 525.67 (M+23)

EP-001190 KM-36

Using substantially the same procedure as for EP-001214, (0.071 g, 0.423 mmol) of phenylsulfanyl-acetic acid and EP-001496 (0.150 g, 0.423 mmol) were dissolved in 2.5 mL of dry CH$_2$Cl$_2$. HOBT (0.063 g, 0.465 mmol) was added followed by EDCI (0.089 g, 0.465 mmol). NMM (0.142 g 0.154 mL, 1.40 mmol) was added and the reaction stirred at room temperature overnight. The residue was washed with 1 N HCL, sat'd NaHCO$_3$, water and brine, dried with Na$_2$SO$_4$. The solvent was removed in vacuo to give an oily residue which was subjected to column chromatography (silica gel, 70:30 ethyl acetate:hexanes) which provided 0.120 g, 56.2% yield as a white solid $^1$H NMR (300 MHz, CDCl$_3$): 7.21 (m, 14H), 6.99 (d, 1H), 5.75 (s, 1H), 4.11 (m, 1H), 4.40 (dd, 2H), 3.29 (m, 2H), 2.96 (dd, 1H), 2.87 (m, 1H), 2.68 (m, 2H), 1.80 (m, 2H), 1.45 (s, 9H) ESMS: 505.67(M+1), 527.63 (M+23)

EP-001192 KM-36-114

Using substantially the same procedure as for EP-001214, (0.064 g, 0.423 mmol) of phenylamino-acetic acid and EP-001496 (0.150 g, 0.423 mmol) were dissolved in 2.5 mL of dry CH$_2$Cl$_2$. HOBT (0.063 g, 0.465 mmol) was added followed by EDCI (0.089 g, 0.465 mmol). NMM (0.142 g 0.154 mL, 1.40 mmol) was added and the reaction stirred at room temperature overnight. The residue was washed with 1 N HCL, sat'd NaHCO$_3$, water and brine, dried with Na$_2$SO$_4$. The solvent was removed in vacuo to give an oily residue which was subjected to column chromatography (silica gel, 70:30 ethyl acetate:hexanes) which provided 0.110 g, 53% yield as a white solid ESMS: 488.72 (M+1), 510.69 (M+23)

EP-001210 KM-36-132

Using substantially the same procedure as for EP-001214, (0.074 g, 0.347 mmol) of (2,6-dimethoxy-phenoxy)-acetic acid and EP-001496 (0.123 g, 0.347 mmol) were dissolved in 1.75 mL of dry DMP. EDCI (0.073 g, 0.382 mmol) was added followed by NMM (0.116 g 0.123 mL, 1.14 mmol) and the reaction stirred at room temperature overnight. The residue was washed with 1 N HCL, sat'd NaHCO$_3$, water and brine, dried with Na$_2$SO$_4$. The solvent was removed in vacuo to give an oily residue that was subjected to column chromatography (silica gel, 70:30 ethyl acetate:hexanes) that provided 0.031 g, 16% yield as a white solid. $^1$H NMR (300 MHz, CDCl$_3$): 7.98(m, 1H), 7.16 (m, 12H), 6.55 (m, 2H), 5.80 (s, 1H), 4.39 (m, 2H), 4.13 (m, 1H), 3.71 (2, 6H), 3.43 (m, 1H), 2.97 (m, 2H), 2.79 (m, 2H), 1.87 (m, 2H), 1.45 (s, 9H) ESMS: 549.81 (M+1), 571.76 (M+23)

EP-001204

Using substantially the same procedure as for EP-001214, (0.062 g, 0.282 mmol) of (2-trifluoromethyl-phenoxy)-acetic acid and EP-001496 (0.100 g, 0.282 mmol) were dissolved in 1.5 mL of dry CH$_2$Cl$_2$. HOBT (0.042 g, 0.310 mmol) was added followed by EDCI (0.059 g, 0.310 mmol). NMM (0.094 g 0.102 mL, 0.931 mmol) was added and the reaction stirred at room temperature overnight. The residue was washed with 1 N HCL, sat'd NaHCO$_3$, water and brine, dried with Na$_2$SO$_4$. The solvent was removed in vacuo to give an oily residue that was subjected to column chromatography (silica gel, 70:30 ethyl acetate:hexanes) that provided 0.0716 g, 46% yield as a white solid. $^1$H NMR (300 MHz, CDCl$_3$): 7.20 (m, 13H), 6.76 (m, 2H), 5.76 (s, 1H), 4.39 (m, 2H), 4.23 (m, 2H), 3.41 (m, 1H), 2.96 (m, 2H), 2.70

(m, 2H), 1.82 (m, 2H), 1.42 (s, 9H) ESMS: 557.54 (M+1), 579.51 (M+23)

EP-001203

Using substantially the same procedure as for EP-001214, (0.062 g, 0.282 mmol) of (2,6-dichloro-phenoxy)-acetic acid and 8 (0.100 g, 0.282 mmol) were dissolved in 1.5 mL of dry $CH_2Cl_2$. HOBT (0.042 g, 0.310 mmol) was added followed by EDCI (0.059 g, 0.310 mmol). NMM (0.094 g 0.102 mL, 0.931 mmol) was added and the reaction stirred at room temperature overnight. The residue was washed with 1 N HCL, sat'd $NaHCO_3$, water and brine, dried with $Na_2SO_4$. The solvent was removed in vacuo to give an oily residue that was subjected to column chromatography (silica gel, 70:30 ethyl acetate:hexanes) that provided 0.0675 g, 43% yield as a white solid. $^1$H NMR (300 MHz, $CDCl_3$): 7.20 (m, 12H), 6.99 (m, 1H), 5.79 (s, 1H), 4.35 (dd, 2H), 4.24 (m, 1H), 3.48 (m, 1H), 3.11 (dd, 1H), 2.94 (m, 1H), 2.82 (m, 2H), 1.94 (m, 2H), 1.44 (s, 9H) ESMS: 557.62 (M+1), 579.6 (M+23)

EP-001202

Using substantially the same procedure as for EP-001214, (0.110 g, 0.564 mmol) of (2,4,6-trimethyl-phenoxy)-acetic acid and EP-001496 (0.200 g, 0.564 mmol) were dissolved in 3.0 mL of dry $CH_2Cl_2$. HOBT (0.084 g, 0.621 mmol) was added followed by EDCI (0.119 g, 0.621 mmol). NMM (0.118 g, 0.205 mL, 1.86 mmol) was added and the reaction stirred at room temperature overnight. The residue was washed with 1 N HCL, sat'd $NaHCO_3$, water and brine, dried with $Na_2SO_4$. The solvent was removed in vacuo to give an oily residue that was subjected to column chromatography (silica gel, 70:30 ethyl acetate:hexanes) that provided 0.0675 g, 43% yield as a white solid. $^1$H NMR (300 MHz, $CDCl_3$): 7.20 (m, 11H), 7.02 (d, 1H), 6.83 (q, 2H), 5.83 (s, 1H), 4.26 (m, 1H), 4.03 (dd, 2H), 3.50 (m, 1H), 3.12 (dd, 1H), 2.96 (m, 1H), 2.82 (m, 2H), 2.17 (s, 3H), 2.04 (s, 6H), 1.96 (m, 2H), 1.44 (s, 9H) ESMS: 531.74 (M+1), 553.73 (M+23)

EP-001201

Using substantially the same procedure as for EP-001214, (0.110 g, 0.564 mmol) of (2,5,6-trimethyl-phenoxy)-acetic acid and EP-000776 (0.200 g, 0.564 mmol) were dissolved in 3.0 mL of dry $CH_2Cl_2$. HOBT (0.084 g, 0.621 mmol) was added followed by EDCI (0.119 g, 0.621 mmol). NMM (0.188 g 0.205 mL, 1.86 mmol) was added and the reaction stirred at room temperature overnight. The residue was washed with 1 N HCL, sat'd $NaHCO_3$, water and brine, dried with $Na_2SO_4$. The solvent was removed in vacuo to give an oily residue which was subjected to column chromatography (silica gel, 70:30 ethyl acetate:hexanes) which provided 0.0996 g, 33% yield as a white solid $^1$H NMR (300 MHz, $CDCl_3$): 7.16 (m, 9H), 6.96 (d, 1H), 6.77 (q, 2H), 5.81 (s, 1H), 4.21 (m, 1H), 3.98 (dd, 2H), 3.45 (m, 1H), 3.06 (dd, 1H), 2.90 (m, 1H), 2.73 (m, 2H), 2.11(s, 3H), 1.93 (m, 8H), 1.39 (s, 9H) ESMS: 531.74 (M+1), 553.73 (M+23)

EP-001228

Using substantially the same procedure as for EP-001214, (0.049 g, 0.310 mmol) of cyclohexyloxy-acetic acid and EP-001496 (0.110 g, 0.310 mmol) were dissolved in 2.5 mL of dry $CH_2Cl_2$. EDCI (0.065 g, 0.341 mmol) was added followed by NMM (0.103 g 0.112 mL, 1.02 mmol) and the reaction stirred at room temperature overnight. The residue was washed with 1 N HCL, sat'd $NaHCO_3$, water and brine, dried with $Na_2SO_4$. The solvent was removed in vacuo to give an oily residue which was subjected to column chromatography (silica gel, 70:30 ethyl acetate:hexanes) which provided 0.078 g, 51% yield as a white solid ESMS: 495.44 (M+1), 517.40 (M+23)

EP-001229

Using substantially the same procedure as for EP-001214, (0.076 g, 0.441 mmol) of (2-methyl-cyclohexyloxy)-acetic acid and EP-001496 (0.156 g, 0.441 mmol) were dissolved in 2.5 mL of dry $CH_2Cl_2$. EDCI (0.093 g, 0.485 mmol) was added followed by NMM (0.147 g, 0.160 mL, 1.46 mmol) and the reaction stirred at room temperature overnight. The residue was washed with 1 N HCL, sat'd $NaHCO_3$, water and brine, dried with $Na_2SO_4$. The solvent was removed in vacuo to give an oily residue which was subjected to column chromatography (silica gel, 70:30 ethyl acetate:hexanes) which provided 0.106 g, 47% yield as a white solid ESMS: 509.47 (M+1), 531.42 (M+23)

EP-001230

Using substantially the same procedure as for EP-001214, (0.050 g, 0.268 mmol) of (2,6-dimethyl-cyclohexyloxy)-acetic acid and EP-001496 (0.095. g, 0.268 mmol) were dissolved in 2.5 mL of dry $CH_2Cl_2$. EDCI (0.057 g, 0.295 mmol) was added followed by NMM (0.089 g, 0.097 mL, 0.884 mmol) and the reaction stirred at room temperature overnight. The residue was washed with 1 N HCL, sat'd $NaHCO_3$, water and brine, dried with $Na_2SO_4$. The solvent was removed in vacuo to give an oily residue which was subjected to column chromatography (silica gel, 70:30 ethyl acetate:hexanes) which provided 0.0814 g, 59% yield as a white solid ESMS: 523.49 (M+1), 545.46 (M+23)

EP-001231

Using substantially the same procedure as for EP-001214, (0.059 g, 0.403 mmol) of 1-ethyl-propoxy acetic acid and EP-001496 (0.139 g, 0.403 mmol) were dissolved in 2.5 mL of dry $CH_2Cl_2$. EDCI (0.085 g, 0.443 mmol) was added followed by NMM (0.135 g, 0.146 mL, 1.33 mmol) and the reaction stirred at room temperature overnight. The residue was washed with 1 N HCL, sat'd $NaHCO_3$, water and brine, dried with $Na_2SO_4$. The solvent was removed in vacuo to give an oily residue which was subjected to column chromatography (silica gel, 70:30 ethyl acetate:hexanes) which provided 0.0947 g, 49% yield as a white solid ESMS: 483.44 (M+1), 505.41 (M+23)

EP-001154

Using substantially the same procedure as for EP-001214, (0.029 g, 0.226 mmol) of 3-methyl-isoxazole-4-carboxylic acid and EP-000776 (0.080 g, 0.226 mmol) were dissolved in 1.5 mL of dry $CH_2Cl_2$. HOBT (0.034 g, 0.249 mmol) was added followed by EDCI (0.048 g, 0.249 mmol). NMM (0.075 g 0.082 mL, 0.746 mmol) was added and the reaction stirred at room temperature overnight. The residue was washed with 1 N HCL, sat'd $NaHCO_3$, water and brine, dried with $Na_2SO_4$. The solvent was removed in vacuo to give an oily residue that was subjected to column chromatography (silica gel, 70:30 ethyl acetate:hexanes) that provided 0.0249 g, 24% yield as a white solid. ESMS: 464.47 (M+1), 486.46 (M+23)

N-((1S,2R)-1-Benzyl-2-hydroxy-but-3-enyl)-2-2(2,6-dimethyl-phenoxy-)acetatnide

Using essentially the same procedure for the preparation of EP-000244, ((1S,2R)-1-benzyl-2-hydroxybut-3-enyl) carbarnic acid tert-butyl ester (0.31 g) was added a solution of 8M HCl in dioxane (15 mL) the residue was dissolved in $CH_2Cl_2$ (7.5 mL) and reacted with N-methylmorpholine (0.36 mL), EDCI (0.234 g), HOBT (0.145 g) and the phenoxyacetic acid (0.20 g). The residue was purified by flash chromatography (silica gel, gradient 10% EtOAc/hexanes to 40% EtOAc/hexanes). The title compound was obtained as an amorphous solid (0188 g, 50%)

EP-001239

Using essentially the same procedure for the preparation of EP-000188, N-((1S,2R)-1-Benzyl-2-hydroxy-but-3-enyl)-2-2(2,6-dimethyl-phenoxy-)acetamide (0.150 g) was combined with 0.213 g of N-tert-butyl-2-fluoro-6-iodobenzamide, bis(benzonitrile)dichloro palladium(II) (0.0254 g), sodium acetate (0.45 g), and N,N-dimethylglycine (0.0911 g) were combined in N-methylpyrrolidinone (3 mL). The resulting material was chromatographed (silica gel) using the a gradient from 20% EtOAc in hexanes to 60% EtOAc in hexanes. An off-white amorphous solid was obtained in 32% yield The above material was then reduced using essentially the same procedure as EP-000776. Thus 0.067 g of the above material, 0.02 g of 10% Pd on carbon and 3 mL of EtOH were hydrogenated. The resulting material was purified by flash chromatography (silica gel, gradient 10% EtOAc/hexanes to 40% ETOAc/hexanes) to give 0.048 g (71%) of a white solid. ESMS: 535.46 (M+1), 557.44 (M+23)

EP-001238

Using essentially the same procedure for the preparation of EP-000188, N-((1S,2R)-1-Benzyl-2-hydroxy-but-3-enyl)-2-2(2,6-dimethyl-phenoxy-)acetamide (0.150 g) was combined with 0.21 g of N-tert-butyl-3-methyl-2-iodobenzamide, bis(benzonitrile)dichloro palladium(II) (0.0254 g), sodium acetate (0.45 g), and N,N-dimethylglycine (0.0911 g) were combined in N-methylpyrrolidinone (3 mL). The resulting material was purified by flash chromatography (silica gel, gradient 20% EtOAc/hexanes to 80% ETOAc/hexanes). An off-white amorphous solid was obtained in 36% yield The above material was then reduced using essentially the same procedure as EP-000776. Thus 0.073 g of the above material, 0.02 g of 10% Pd on carbon and 4 mL of EtOH were hydrogenated. The resulting material was purified by flash chromatography (silica gel, gradient 20% EtOAc/hexanes to 40% ETOAc/hexanes) to give 0.050 g (68%) of a white solid. ESMS: 531.42 (M+1)

EP-001249

Using essentially the same procedure for the preparation of EP-000188, N-((1S,2R)-1-Benzyl-2-hydroxy-but-3-enyl)-2-2(2,6-dimethyl-phenoxy-)acetamide (0.100 g) was combined with 0.135 g of N-tert-butyl-2-methyl-6-iodobenzamide, bis(benzonitrile)dichloro palladium(II) (0.017 g), sodium acetate (0.967 g), and N,N-dimethylglycine (0.0608 g) were combined in N-methylpyrrolidinone (2 mL). The resulting material was purified by flash chromatography (silica gel, gradient 30% EtOAc/hexanes to 50% ETOAc/hexanes). An off-white amorphous solid was obtained in 63.5% yield The above material was then reduced using essentially the same procedure as EP-000776. Thus 0.076 g of the above material, 0.02 g of 10% Pd on carbon and 4 mL of EtOH were hydrogenated. The resulting material was purified by flash chromatography (silica gel, gradient 20% EtOAc/hexanes to 40% ETOAc/hexanes) to give 71% of a white solid. ESMS: 531.42 (M+1)

EP-001237

Using essentially the same procedure for the preparation of EP-000188, N-((1S,2R)-1-Benzyl-2-hydroxy-but-3-enyl)-2-2(2,6-dimethyl-phenoxy-)acetamide (0.150 g) was combined with 0.210 g of N-tert-butyl-3-methyl-6-iodobenzamide, bis(benzonitrile)dichloro palladium(II) (0.026 g), sodium acetate (0.14 g), and N,N-dimethylglycine (0.091 g) were combined in N-methylpyrrolidinone (3 mL). The resulting material was purified by flash chromatography (silica gel, gradient 30% EtOAc/hexanes to 70% ETOAc/hexanes). An off-white amorphous solid was obtained in 48% yield The above material was then reduced using essentially the same procedure as EP-000776. Thus 0.080 g of the above material, 0.02 g of 10% Pd on carbon and 4 mL of EtOH were hydrogenated The resulting material was purified by flash chromatography (silica gel, gradient 20% EtOAc/hexanes to 40% EtOAc/hexanes) to give 0.064 g (80%) of a white solid. ESMS: 531.50 (M+1)

EP-000987

Using essentially the same procedure as for the preparation of EP-000244, EP-000776 (0.10 g, 0.22 mmol) was first reacted with 8M HCl in dioxane solution (25 mL) followed by NMM (0.01 mL), EDCI (0.046 g, 0.24 mmol), HOBT (0.033 g, 0.24 mmol) and (2,6-dimethyl-phenoxy)-acetic acid (0.04 g, 0.22 mmol) in $CH_2Cl_2$ to give the title compound as an amorphous solid (0.023 g, 22%) ESMS: 517.94 (M+1).

EP-001219

Using essentially the same procedure as for the preparation of EP-000244, 0.070 g (0.19 mmol) of the TBDMS ether of EP-000776 (TBDMSCl, DMF, imidazole) was fist reacted with 8M HCl in dioxane solution (5 mL) followed by NMM (0.12 mL), EDCI (0.074 g), HOBT (0.052 g) and (R)-2-hydroxy-4-methylpentanoic acid (0.046 g) in DMF/$CH_2Cl_2$ to give the title compound as an amorphous solid (0.03 g, 19%) ESMS: 469.66 (M+1).

EP-001206

Using substantially the same procedure as for EP-001214, (0.041 g, 0.213 mmol) of (2-allyl-6-methyl-phenoxy)acetic acid and EP-001496 (0.070 g, 0.197 mmol) was reacted with HOBT (0.042 g, 0.310 mmol), EDCI (0.059 g, 0.310 mmol) and NMM (0.094 g 0.102 mL, 0.931 mmol) in $CH_2Cl_2$. The resulting material was purified by column chromatography (silica gel, 30% ethyl acetate in hexanes) that provided 0.082 g, 80% yield as a white solid. $^1$H NMR (300 MHz, $CDCl_3$): d 7.08–7.35 (m, 9H); 6.91 (m, 3H); 5.78 (m, 1H); 5.72 (S, 1H); 5.33 (s, 1H); 4.94 (d, J=9.6, 1H); 4.85 (d, J=17.2, 1H); 4.21 (m, 1H); 4.03 (d, J=14.8, 1H); 3.93 (d, J=14.8, 1H); 3.44 (m, 1H); 3.16 (d, J=5.2, 2H); 3.06 (dd, J=4.0, 14.0, 1H); 2.91 (m, 1H); 2.75 (m, 2H); 2.05 (s, 3H), 1.40 (s, 9H)

EP-001006

Diphenylcarbamyl chloride (0.054 mmol) and EP-001496 (0.054 mmol) were placed in a vial, anhydrous $CH_2Cl_2$ (0.50 mL) was added. DIEA (0.013 g, 0.018 mL, 0.108 mmol) was added and the reaction was placed on a shaker overnight. The solvent was removed in vacuo and the residue was taken up in 50:50 (ethyl acetate:hexanes) and put through a plug of silica and $MgSO_4$, the solvent was removed in vacuo and the compounds were subjected to LC/MS. ESMS: 550(M+1)

Biological Assay for Inhibition of Microbial Expressed Viral Protease

The inhibition constants against HIV-1 protease were measured using the method described by M. V. Toth and G. R. Marshall, *Int. J. Peptide protein Res.,* 1990, 544. The method described M. W. Pennington et al., Peptides 1990, Gimet, E. and D. Andrew, Eds., Escom; Leiden, Netherlands (1990) may also be used. The potency is measured as $IC_{50}$ in μM. The person of skill would accept these tests as predictive of the compounds' utility in vivo to treat HIV infected patients.

We claim:
1. A compound of formula:

[chemical structures]

wherein:
R$^1$ is chosen from the group consisting of C$_1$–C$_{20}$ alkyl, substituted C$_1$–C$_{20}$ alkyl, aryl, alkylaryl, substituted alkylaryl, C$_3$–C$_{10}$ oxaalkyl, substituted aryl;
R$^2$ is chosen from the group consisting of C$_1$–C$_{10}$ hydrocarbon and substituted aryl;
A is

[chemical structure]

wherein r→designates the point of attachment of R$^1$ and n→designates the point of attachment to N;

[chemical structure]

is phenyl containing from 0 to 3 substituents chosen from lower alkyl, lower alkoxy, lower alkylthio, hydroxy, mercapto, cyano, carboxy, lower alkoxycarbonyl, (lower alkoxycarbonyl)lower alkoxy, lower alkylaminocarbonyl, amino, lower alkylamino, di(lower alkyl)amino, nitro, halo and haloalkyl;
R$^5$ is chosen from the group consisting of hydrogen, alkyl, aryl and substituted aryl;
R$^6$ and R$^7$ are chosen from the group consisting of hydrogen, halogen and lower alkyl;
D is —C(O) or —NHC(O)—;
E is chosen from the group consisting of C$_5$–C$_8$ alkyl and NR$^{10}$R$^{11}$;

R$^{10}$ is hydrogen or lower alkyl;
R$^{11}$ is chosen from C$_1$–C$_{10}$ hydrocarbon, substituted aryl and substituted alkyl; and
Y is —O—,
or a pharmaceutically acceptable salt thereof.

2. A compound according to claim 1 wherein

[chemical structure]

is phenyl.

3. A compound according to claim 2 wherein

[chemical structure]

is

[chemical structure]

wherein
R$^{12}$ is chosen from the group consisting of hydrogen, halogen, lower alkyl, hydroxy, lower alkoxy, nitro and lower alkoxy;
R$^{13}$ is chosen from the group consisting of hydrogen, halogen, lower alkyl, hydroxy and lower alkoxy;
R$^{14}$ is chosen from the group consisting of hydrogen, halogen, lower alkyl, hydroxy and lower alkoxy; and
c→ and d→ designate the points of attachment to the carbon chain and D respectively.

4. A compound according to claim 1 wherein D is —C(O)—.

5. A compound according to claim 1 wherein R$^2$ is phenyl, ethyl, propyl, or butyl.

6. A pharmaceutical composition comprising a pharmaceutically acceptable carrier and a compound according to claim 1, or a pharmaceutically acceptable salt or solvate thereof.

7. A pharmaceutical composition according to claim 6 comprising at least one additional antiviral agent.

* * * * *